United States Patent
Kang et al.

(10) Patent No.: US 11,196,009 B2
(45) Date of Patent: Dec. 7, 2021

(54) FLUORENE DERIVATIVE, ORGANIC LIGHT EMITTING DEVICE USING SAME, AND MANUFACTURING METHOD THEREFOR

(71) Applicant: LG Chem, Ltd., Seoul (KR)

(72) Inventors: Esder Kang, Daejeon (KR); Young Kwang Kim, Daejeon (KR); Jaesoon Bae, Daejeon (KR); Jae Hak Jeong, Daejeon (KR); Jiyeon Shin, Daejeon (KR); Seog Jae Seo, Daejeon (KR); Jaechol Lee, Daejeon (KR); Sungkyoung Kang, Daejeon (KR); Leehyeon Baek, Daejeon (KR)

(73) Assignee: LG Chem, Ltd.

( * ) Notice: Subject to any disclaimer, the term of this patent is extended or adjusted under 35 U.S.C. 154(b) by 374 days.

(21) Appl. No.: 16/326,765

(22) PCT Filed: Nov. 24, 2017

(86) PCT No.: PCT/KR2017/013540
§ 371 (c)(1),
(2) Date: Feb. 20, 2019

(87) PCT Pub. No.: WO2018/097654
PCT Pub. Date: May 31, 2018

(65) Prior Publication Data
US 2019/0214568 A1 Jul. 11, 2019

(30) Foreign Application Priority Data
Nov. 25, 2016 (KR) .......... 10-2016-0158512

(51) Int. Cl.
*H01L 51/00* (2006.01)
*C07D 307/91* (2006.01)
(Continued)

(52) U.S. Cl.
CPC ........ *H01L 51/0061* (2013.01); *C07C 211/54* (2013.01); *C07C 211/58* (2013.01);
(Continued)

(58) Field of Classification Search
None
See application file for complete search history.

(56) References Cited

U.S. PATENT DOCUMENTS

2007/0102695 A1* 5/2007 Inbasekaran ........... C08G 73/22
257/40
2008/0166566 A1 7/2008 Prakash et al.
(Continued)

FOREIGN PATENT DOCUMENTS

JP 3884557 B2 2/2007
JP 2007220772 A 8/2007
(Continued)

OTHER PUBLICATIONS

Scheler et al. "Synthesis and Properties of Alternating Fluorene-Based Oligomers for Sub-μm Photopatterning." Macromolecular Chemistry and Physics 211, No. 19 (2010): 2081-2089. (Year: 2010).*

(Continued)

*Primary Examiner* — Robert S Loewe
(74) *Attorney, Agent, or Firm* — Lerner, David, Littenberg, Krumholz & Mentlik, LLP

(57) ABSTRACT

The present specification provides a coating composition including a fluorene derivative, an organic light emitting device formed using the coating composition, and a method for manufacturing the same.

20 Claims, 4 Drawing Sheets

| 701 |
|:---:|
| 601 |
| 501 |
| 401 |
| 301 |
| 201 |
| 101 |

(51) Int. Cl.
*C07C 211/60* (2006.01)
*C07C 211/54* (2006.01)
*C07C 211/58* (2006.01)
*C07D 333/76* (2006.01)
*H01L 51/50* (2006.01)
*H01L 51/56* (2006.01)

(52) U.S. Cl.
CPC .......... *C07C 211/60* (2013.01); *C07D 307/91* (2013.01); *C07D 333/76* (2013.01); *H01L 51/006* (2013.01); *H01L 51/0026* (2013.01); *H01L 51/0052* (2013.01); *H01L 51/0059* (2013.01); *H01L 51/0073* (2013.01); *H01L 51/0074* (2013.01); *H01L 51/5088* (2013.01); *H01L 51/56* (2013.01); *C07C 2603/18* (2017.05); *H01L 51/506* (2013.01); *H01L 51/5056* (2013.01)

(56) References Cited

U.S. PATENT DOCUMENTS

| | | |
|---|---|---|
| 2009/0051281 A1 | 2/2009 | Inoue et al. |
| 2010/0019657 A1 | 1/2010 | Eum et al. |
| 2011/0089411 A1 | 4/2011 | Xia et al. |
| 2015/0094437 A1 | 4/2015 | Caille et al. |

FOREIGN PATENT DOCUMENTS

| | | |
|---|---|---|
| JP | 2011173973 A | 9/2011 |
| JP | 2012111719 A | 6/2012 |
| KR | 20060127853 A | 12/2006 |
| KR | 20090104079 A | 10/2009 |
| KR | 20110037972 A | 4/2011 |
| KR | 20120112277 A | 10/2012 |
| KR | 20140107594 A | 9/2014 |
| KR | 20140132562 A | 11/2014 |
| TW | 200936730 A | 9/2009 |
| WO | 2016026266 A1 | 2/2016 |

OTHER PUBLICATIONS

Abraham et al., "Cross-linkable fluorene-diphenylamine derivatives for electrochromic applications," ACS Applied Materials & Interfaces, vol. 7 (45), Oct. 23, 2015, pp. 25424-25433.
International Search Report for PCT/KR2017/013540 dated Oct. 12, 2018.
Taiwanese Search Report for TW10720667710 dated Jul. 25, 2018.

* cited by examiner

[FIG. 1]
| 701 |
| :---: |
| 601 |
| 501 |
| 401 |
| 301 |
| 201 |
| 101 |
[FIG. 2]
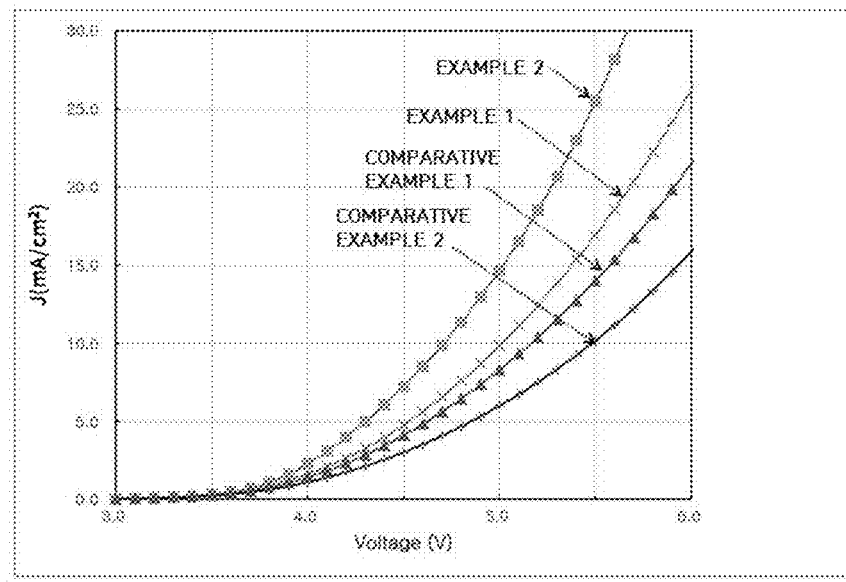

[FIG. 3]
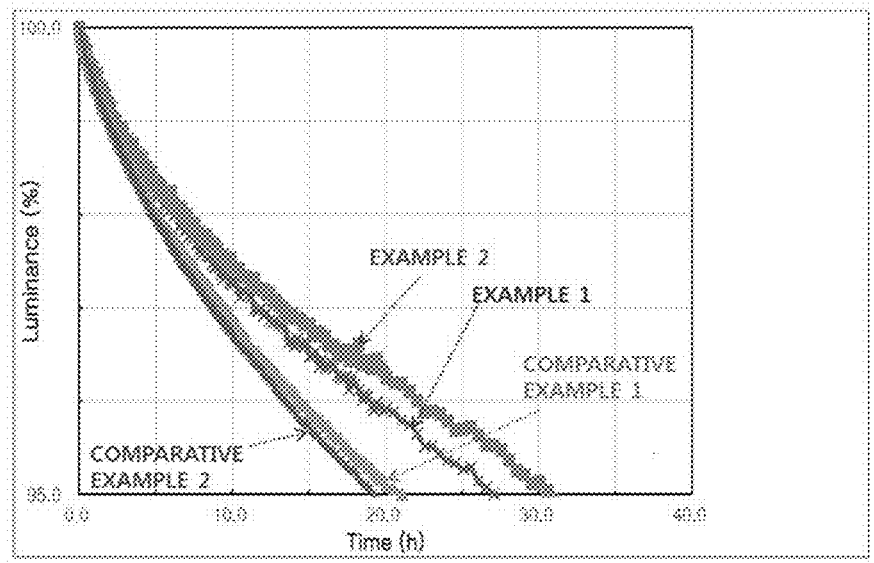
[FIG. 4]
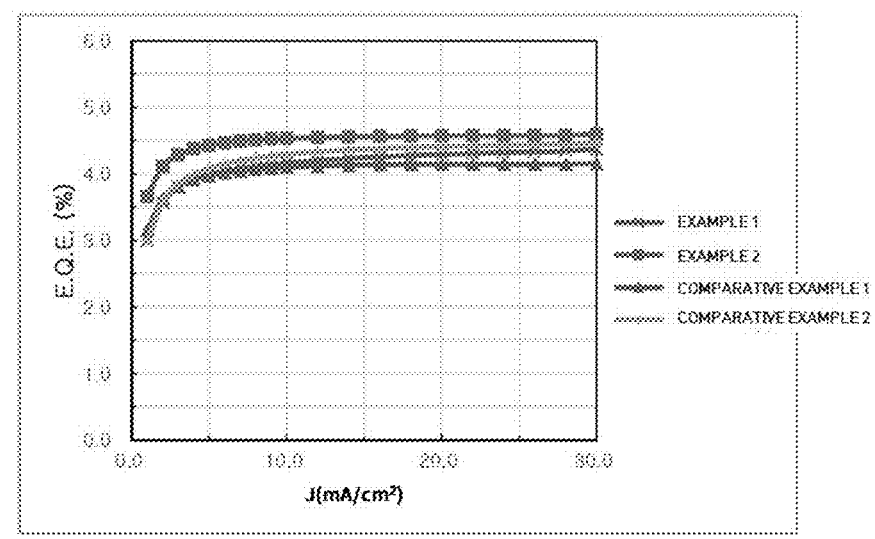

[FIG. 5]
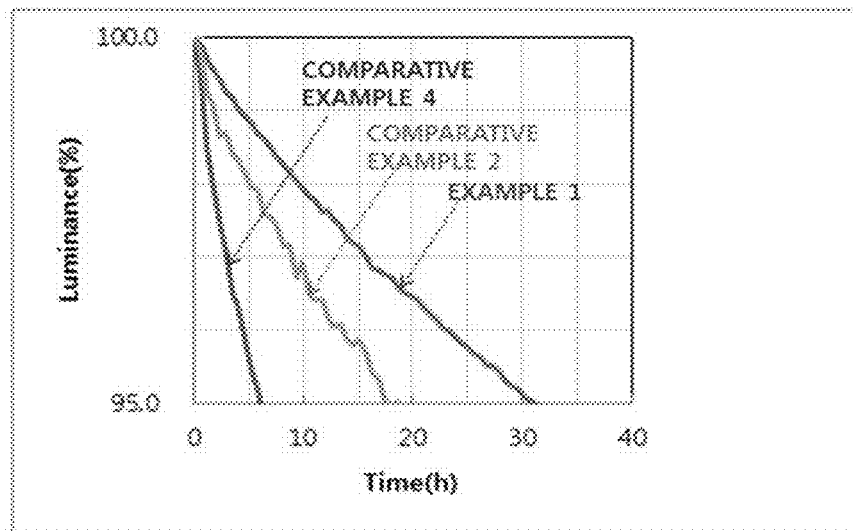
[FIG. 6]
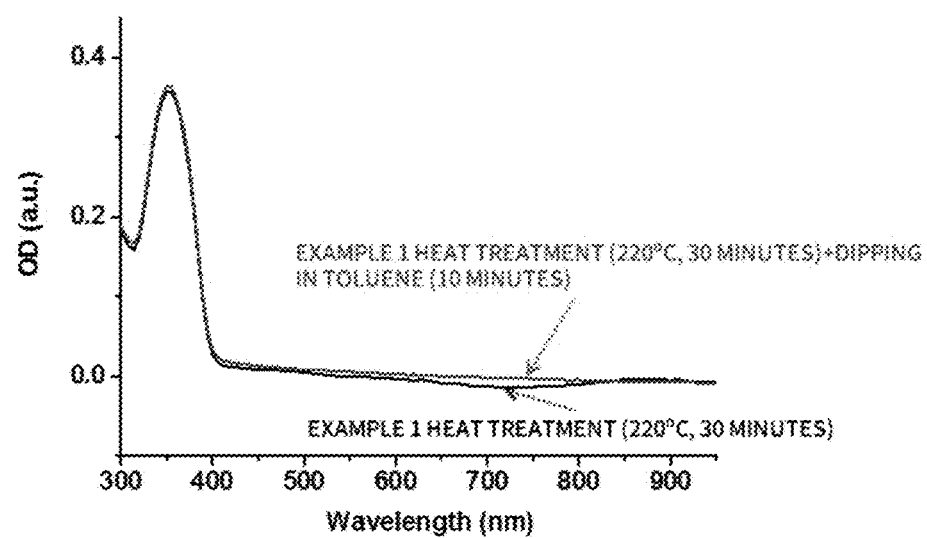

[FIG. 7]
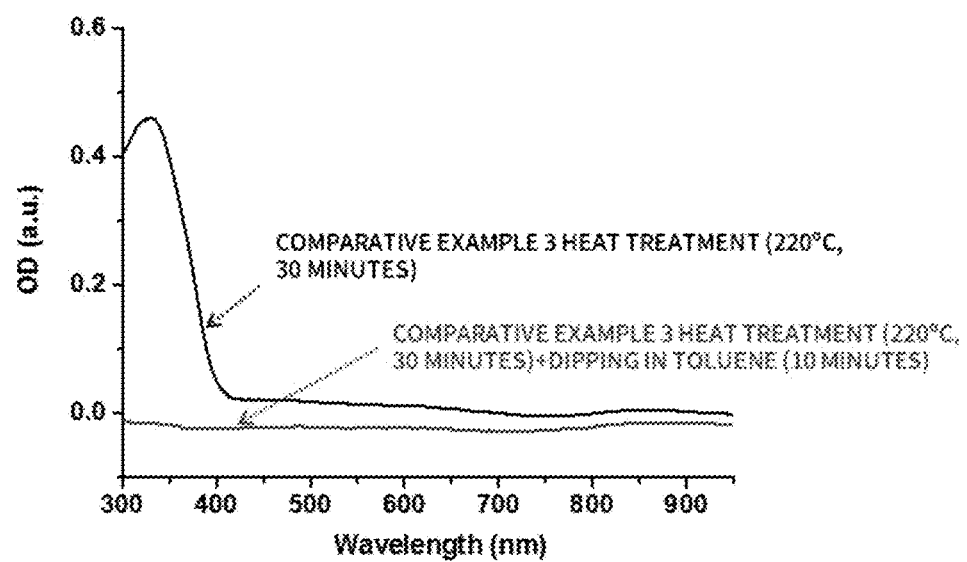

FLUORENE DERIVATIVE, ORGANIC LIGHT EMITTING DEVICE USING SAME, AND MANUFACTURING METHOD THEREFOR

TECHNICAL FIELD

This application claims priority to and the benefits of Korean Patent Application No. 10-2016-0158512, filed with the Korean Intellectual Property Office on Nov. 25, 2016, the entire contents of which are incorporated herein by reference.

The present specification relates to a fluorene derivative, a coating composition including the fluorene derivative, an organic light emitting device formed using the coating composition, and a method for manufacturing the same.

BACKGROUND ART

An organic light emission phenomenon is one of examples converting current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic light emitting device using such a principle may be generally formed with a cathode, an anode, and an organic material layer placed therebetween, for example, an organic material layer including a hole injection layer, a hole transfer layer, a light emitting layer and an electron transfer layer.

Materials used in an organic light emitting device are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting layer material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferred that materials used in an organic light emitting device additionally have properties as follows.

First, materials used in an organic light emitting device preferably have excellent thermal stability. This is due to joule heating produced by charge migration in the organic light emitting device. N,N'-di(naphthalene-1-yl)-N,N'-diphenylbenzidine (NPB) normally used as a hole transfer layer material currently has a glass transition temperature of 100° C. or lower, and has a problem in that it is difficult to use in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a HOMO or LUMO energy level. PEDOT:PSS currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long life time.

In addition thereto, materials used in an organic light emitting device need to have excellent chemical stability, charge mobility, and interface properties with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials need to improve an interface with electrodes including metals or metal oxides.

Recently, attempts to develop an organic light emitting device using a solution process, particularly, an inkjet process, replacing an existing deposition process have been made. This may significantly reduce process costs for an organic light emitting device. In the earlier days, it was planned to develop an organic light emitting device by coating all organic light emitting device layers using a solution process, however, this has a limit with current technologies, and studies on a hybrid process of, in a normal structure form, applying a solution process for only a hole injection layer (HIL), a hole transfer layer (HTL) and a light emitting layer (EML), and using an existing deposition process for later processes have been in progress. In addition, organic light emitting materials having a polymer form have been much used in the art to increase coatibility, however, considerable monomer OLED materials are currently under development due to problems of batch to batch variation and purity of a polymer itself.

PRIOR ART DOCUMENTS

Patent Documents

Korean Patent Application Laid-Open Publication No. 2012-0112277

DISCLOSURE

Technical Problem

The present specification is directed to providing a fluorene derivative, a coating composition including the fluorene derivative, an organic light emitting device formed using the coating composition, and a method for manufacturing the same.

Technical Solution

One embodiment of the present specification provides a fluorene derivative, a compound represented by the following Chemical Formula 1:

[Chemical Formula 1]

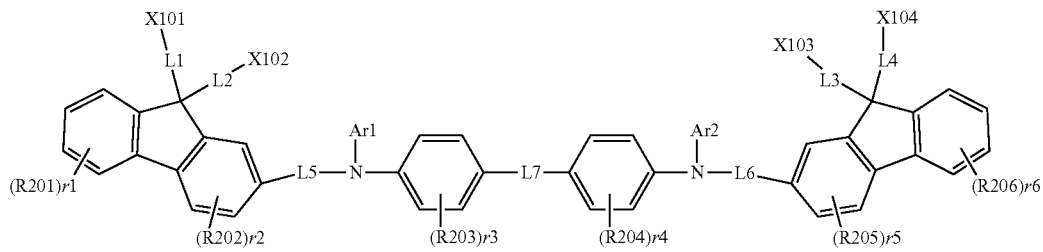

in Chemical Formula 1,

L1 to L4 are the same as or different from each other, and each independently a direct bond; a substituted or unsubstituted alkylene group; a substituted or unsubstituted cycloalkylene group; a substituted or unsubstituted arylene group; or a substituted or unsubstituted heteroarylene group, L5 and L6 are the same as or different from each other, and each independently a substituted or unsubstituted arylene group, L7 is a direct bond, O, S, SO, $SO_2$, or a substituted or unsubstituted alkylene group, R201 to R206 are the same as or different from each other, and each independently hydrogen; deuterium; a silyl group; a substituted or unsubstituted alkyl group; a substituted or unsubstituted alkenyl group; a substituted or unsubstituted ester group; a substituted or unsubstituted cycloalkyl group; a substituted or unsubstituted aryl group; or a substituted or unsubstituted heteroaryl group, Ar1 and Ar2 are the same as or different from each other, and each independently a substituted or unsubstituted alkyl group; a substituted or unsubstituted cycloalkyl group; a substituted or unsubstituted aryl group; or a heteroaryl group, X101 to X104 are the same as or different from each other, and each independently hydrogen; a thermo-curable group; or a photo-curable group, and at least one of X101 and X102 and at least one of X103 and X104 are each a thermo-curable group; or a photo-curable group, r1, r3, r4 and r6 are each independently an integer of 0 to 4, r2 and r5 are each independently an integer of 0 to 3, and when r1 to r6 are each 2 or greater, substituents in the parentheses are the same as or different from each other.

Another embodiment of the present specification includes a coating composition including the fluorene derivative described above.

Another embodiment of the present specification provides an organic light emitting device including a cathode; an anode; and one or more organic material layers provided between the cathode and the anode, wherein one or more layers of the organic material layers include a cured material of the coating composition described above, and the cured material of the coating composition is in a cured state by heat treatment or light treatment on the coating composition.

Another embodiment of the present specification provides a method for manufacturing an organic light emitting device including preparing a substrate; forming a cathode or an anode on the substrate; forming one or more organic material layers on the cathode or the anode; and forming an anode or a cathode on the organic material layer, wherein the forming of one or more organic material layers includes forming an organic material layer using the coating composition.

Advantageous Effects

A fluorene derivative according to one embodiment of the present specification can be prepared using a solution process, and therefore, large-area devices can be manufactured. The fluorene derivative according to one embodiment of the present specification can be used as a material of an organic material layer of an organic light emitting device, and is capable of providing properties of low driving voltage, high light emission efficiency and excellent life time. The organic material layer formed using the fluorene derivative according to one embodiment of the present specification has excellent chemical resistance and film retention rate.

In addition, by using the fluorene derivative, solubility increases, which leads to advantages of having a wide selection of solvents when preparing an ink of a solution process, and lowering a melting point and a curing temperature.

DESCRIPTION OF DRAWINGS

FIG. 1 illustrates an example of an organic light emitting device according to one embodiment of the present specification.

FIG. 2 is a graph showing a relation between a driving voltage and current density for devices of Examples 1 and 2 and Comparative Examples 1 and 2 of the present specification.

FIG. 3 is a graph showing a relation between a life time and luminance for devices of Examples 1 and 2 and Comparative Examples 1 and 2 of the present specification.

FIG. 4 is a graph showing a relation between current density and external quantum efficiency for devices of Examples and 2 and Comparative Examples 1 and 2 of the present specification.

FIG. 5 is a graph showing a relation between a life time and luminance for devices manufactured in Example 1, Comparative Example 2 and Comparative Example 4 of the present specification.

FIG. 6 is a graph showing wavelength-dependent optical density before/after dipping a device of Example 1 in toluene after heat treating the device.

FIG. 7 is a graph showing wavelength-dependent optical density before/after dipping a device of Comparative Example 3 in toluene after heat treating the device.

REFERENCE NUMERAL

101: Substrate
201: Anode

301: Hole Injection Layer
401: Hole Transfer Layer
501: Light Emitting Layer
601: Electron Transfer Layer
701: Cathode

MODE FOR DISCLOSURE

Hereinafter, the present specification will be described in more detail.

In the present specification, a description of a certain member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

One embodiment of the present specification provides a coating composition for an organic light emitting device including a fluorene derivative represented by Chemical Formula 1. The coating composition for an organic light emitting device including the fluorene derivative represented by Chemical Formula 1 is readily prepared due to excellent solubility, and a uniform coating layer may be formed using the coating composition. In addition, when mixing with a p-doping material used as a hole injection layer, a hole transfer ability is enhanced due to the fluorene derivative, and as a result, a driving voltage decreases, high light emission efficiency is exhibited, and an excellent life time property is obtained.

Hereinafter, substituents of the present specification will be described in detail.

In the present specification,

means a site linking to other substituents.

The term "substitution" in the present specification means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one or more substituents selected from the group consisting of deuterium; a halogen group; a nitrile group; a nitro group; a hydroxyl group; an alkyl group; an alkoxy group; an alkenyl group; a silyl group; an ester group; a cycloalkyl group; an aryl group; an amine group; an arylamine group and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, examples of the halogen group may include fluorine, chlorine, bromine or iodine.

In the present specification, the alkyl group may be linear or branched, and although not particularly limited thereto, the number of carbon atoms is preferably from 1 to 50. Specific examples thereof may include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the alkoxy group may be linear, branched or cyclic. The number of carbon atoms of the alkoxy group is not particularly limited, but is preferably from 1 to 40. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenxyloxy and the like, but are not limited thereto.

The alkyl group, the alkoxy group and other substituents including an alkyl group part described in the present specification include both a linear or branched form.

In the present specification, the alkenyl group may be linear or branched, and although not particularly limited thereto, the number of carbon atoms is preferably from 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, in the ester group, the oxygen of the ester group may be substituted with a linear, branched or cyclic alkyl group having 1 to 25 carbon atoms or an aryl group having 6 to 30 carbon atoms. Specifically, compounds having the following structural formulae may be included, however, the ester group is not limited thereto.

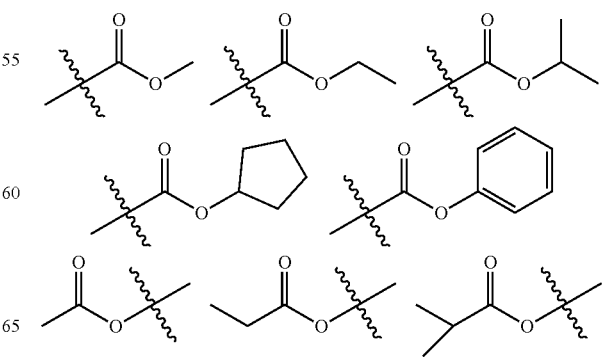

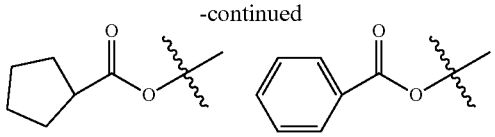

In the present specification, the cycloalkyl group is not particularly limited, but preferably has 3 to 60 carbon atoms, and according to one embodiment, the number of carbon atoms of the cycloalkyl group is from 3 to 40. According to another embodiment, the number of the carbon atoms of the cycloalkyl group is from 3 to 20. According to another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may include a phenyl group, a biphenyl group, a terphenyl group and the like, but are not limited thereto. Examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and two substituents may bond to each other to form a spiro structure.

When the fluorenyl group is substituted, a substituted fluorenyl group including a spirofluorenyl group such as

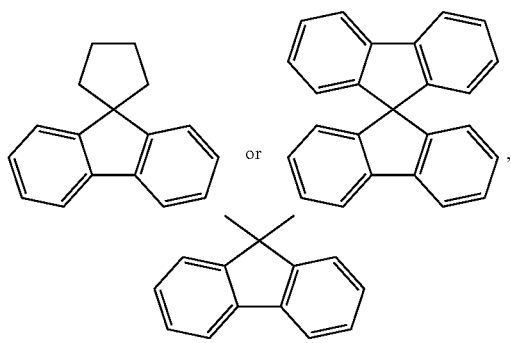

(9,9-dimethylfluorenyl group),

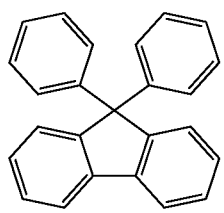 [SMILES: c1ccc(C2(c3ccccc3)c3ccccc3-c3ccccc32)cc1]

(9,9-diphenylfluorenyl group) and the like may be included. However, the structure is not limited thereto.

The aryl group may be substituted with an alkyl group to function as an arylalkyl group. The alkyl group may be selected from among the examples described above.

In the present specification, the heterocyclic group is a heterocyclic group including one or more of N, O, P, S, Si and Se as a heteroatom, and although not particularly limited thereto, the number of carbon atoms is preferably from 1 to 60. According to one embodiment, the number of carbon atoms of the heterocyclic group is from 1 to 30. Examples of the heterocyclic group may include a pyridyl group, a pyrrole group, a pyrimidyl group, a pyridazinyl group, a furanyl group, a thiophene group, an imidazole group, a pyrazole group, an oxazole group, an isoxazole group, a triazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a thiazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophene group, a benzofuranyl group, a dibenzothiophene group, a dibenzofuranyl group and the like, but are not limited thereto.

The heterocyclic group may be monocyclic or multicyclic, may be aromatic, aliphatic or a fused ring of aromatic and aliphatic.

In the present specification, descriptions on the heterocyclic group provided above may be applied to the heteroaryl group except for being aromatic.

In the present specification, the number of carbon atoms of the amine group is not particularly limited, but is preferably from 1 to 30. The amine group may be substituted with the alkyl group, the aryl group, the heterocyclic group, the alkenyl group, the cycloalkyl group, combinations thereof, and the like described above. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, the arylamine group means an amine group substituted with an aryl group, and the examples described above may be applied to the aryl group.

In the present specification, the alkylene group may be selected from among examples of the alkyl group described above except for being a divalent.

In the present specification, descriptions on the cycloalkyl group provided above may be applied to the cycloalkylene group except for being a divalent.

In the present specification, descriptions on the aryl group provided above may be applied to the arylene group except for being a divalent.

In the present specification, descriptions on the heteroaryl group provided above may be applied to the heteroarylene group except for being a divalent.

According to one embodiment of the present specification, L1 to L4 are the same as or different from each other, and each independently a direct bond; a substituted or unsubstituted alkylene group having 1 to 40 carbon atoms; a substituted or unsubstituted cycloalkylene group having 3 to 60 carbon atoms; a substituted or unsubstituted arylene group having 6 to 60 carbon atoms; or a substituted or unsubstituted heteroarylene group having 2 to 60 carbon atoms.

According to another embodiment, L1 to L4 are the same as or different from each other, and each independently a direct bond; a substituted or unsubstituted alkylene group having 1 to carbon atoms; or a substituted or unsubstituted cycloalkylene group having 3 to 60 carbon atoms.

According to another embodiment, L1 to L4 are the same as or different from each other, and each independently a direct bond; an alkylene group having 1 to 40 carbon atoms; or a cycloalkylene group having 3 to 60 carbon atoms.

According to another embodiment, L1 to L4 are the same as or different from each other, and each independently a direct bond; or an alkylene group having 1 to 40 carbon atoms.

According to another embodiment, L1 to L4 are the same as or different from each other, and each independently an alkylene group having 1 to 40 carbon atoms.

According to another embodiment, L1 to L4 are the same as or different from each other, and each independently an alkylene group having 1 to 20 carbon atoms.

According to another embodiment, L1 to L4 are the same as or different from each other, and each independently an alkylene group having 1 to 5 carbon atoms.

According to one embodiment of the present specification, L5 and L6 are the same as or different from each other, and each independently a substituted or unsubstituted arylene group having 6 to 60 carbon atoms.

According to another embodiment, L5 and L6 are the same as or different from each other, and each independently an arylene group having 6 to 60 carbon atoms.

According to another embodiment, L5 and L6 are the same as or different from each other, and each independently an arylene group having 6 to 30 carbon atoms.

According to another embodiment, L5 and L6 are the same as or different from each other, and each independently a phenylene group; a biphenylylene group; a naphthylene group; or a phenanthrenyl group.

According to another embodiment, L5 and L6 are the same as or different from each other, and each independently a phenylene group; or a biphenylylene group.

According to another embodiment, L5 and L6 are a phenylene group.

According to one embodiment of the present specification, L7 is a direct bond, O, S, SO, $SO_2$, or a substituted or unsubstituted alkylene group.

According to another embodiment, L7 is a direct bond, or an alkylene group having 1 to 40 carbon atoms.

According to another embodiment, L7 is a direct bond.

According to another embodiment, L7 is a linear or branched alkyl group having 1 to 6 carbon atoms.

According to one embodiment of the present specification, R201 to R206 are the same as or different from each other, and each independently hydrogen; deuterium; a substituted or unsubstituted silyl group; a substituted or unsubstituted alkyl group; a substituted or unsubstituted alkenyl group; a substituted or unsubstituted ester group; a substituted or unsubstituted cycloalkyl group; a substituted or unsubstituted aryl group; or a substituted or unsubstituted heteroaryl group.

According to another embodiment, R201 to R206 are the same as or different from each other, and each independently hydrogen; deuterium; a substituted or unsubstituted alkyl group having 1 to 40 carbon atoms; or a substituted or unsubstituted aryl group having 6 to 60 carbon atoms.

According to another embodiment, R201 to R206 are the same as or different from each other, and each independently hydrogen; deuterium; an alkyl group having 1 to 20 carbon atoms; or an aryl group having 6 to 30 carbon atoms.

According to another embodiment, R201 to R206 are hydrogen.

According to one embodiment of the present specification, Ar1 and Ar2 are the same as or different from each other, and each independently a substituted or unsubstituted alkyl group having 1 to 40 carbon atoms; a substituted or unsubstituted cycloalkyl group having 3 to 60 carbon atoms; a substituted or unsubstituted aryl group having 6 to 60 carbon atoms; or a substituted or unsubstituted heteroaryl group.

According to another embodiment, Ar1 and Ar2 are the same as or different from each other, and each independently a substituted or unsubstituted aryl group having 6 to 60 carbon atoms; or a substituted or unsubstituted heteroaryl group having 5 to 60 carbon atoms.

According to another embodiment, Ar1 and Ar2 are the same as or different from each other, and each independently a substituted or unsubstituted aryl group having 6 to 30 carbon atoms; or a substituted or unsubstituted heteroaryl group having 5 to 30 carbon atoms.

According to another embodiment, Ar1 and Ar2 are the same as or different from each other, and each independently an aryl group having 6 to 30 carbon atoms unsubstituted or substituted with an alkyl group; or a heteroaryl group having 5 to 30 carbon atoms unsubstituted or substituted with an alkyl group.

According to another embodiment, Ar1 and Ar2 are the same as or different from each other, and each independently a phenyl group; a biphenyl group; a naphthylenyl group; a phenanthrenyl group; a dimethylfluorenyl group; a dibenzothiophene group; or a dibenzofuranyl group.

According to another embodiment, Ar1 and Ar2 are the same as or different from each other, and each independently a phenyl group; a biphenyl group; a naphthylenyl group; a dimethylfluorenyl group; a dibenzothiophene group; or a dibenzofuranyl group.

In the present specification, the "thermo-curable group or photo-curable group" may mean a reactive substituent crosslinking compounds by being exposed to heat or light. The crosslinking may be produced while radicals produced by decomposing carbon-carbon multiple bonds or cyclic structures through heat treatment or light irradiation are linked.

For example, the thermo-curable group or the photo-curable group is

, and the thermo-curable group or the photo-curable group may be linked to other fluorene derivatives with a structure of

crosslinked by heat treatment of light treatment.

According to one embodiment of the present specification, at least one of X101 and X102 and at least one of X103 and X104 are each a thermo-curable group; or a photo-curable group, and the thermo-curable group or the photo-curable group is selected from among the following structures.

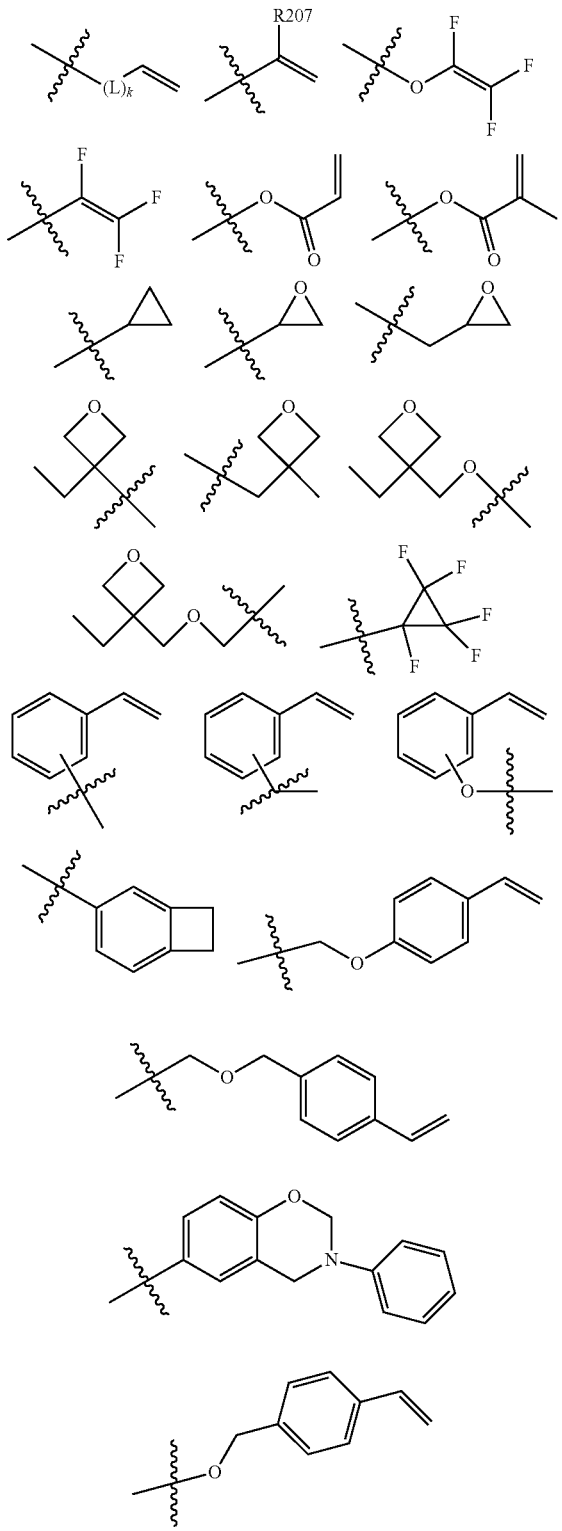
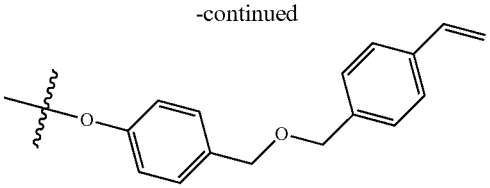

In the structures,

R207 is hydrogen; deuterium; a halogen group; a substituted or unsubstituted alkyl group; a substituted or unsubstituted cycloalkyl group; a substituted or unsubstituted amine group; a substituted or unsubstituted arylamine group; a substituted or unsubstituted silyl group; a substituted or unsubstituted aryl group; or a substituted or unsubstituted heterocyclic group, L is a direct bond; O; S; a substituted or unsubstituted alkylene group; a substituted or unsubstituted arylene group; or a substituted or unsubstituted divalent heterocyclic group, and k is an integer of 1 or 2, and when k is 2, substituents in the parentheses are the same as or different from each other.

In one embodiment of the present specification, R207 is a substituted or unsubstituted alkyl group having 1 to 20 carbon atoms.

According to another embodiment, R207 is an alkyl group having 1 to 20 carbon atoms.

According to another embodiment, R207 is an alkyl group having 1 to 6 carbon atoms.

In one embodiment of the present specification, in the fluorene derivative including a thermo-curable group or a photo-curable group, solvent resistance is strengthened due to the curable group, and therefore, an organic light emitting device may be manufactured using a solution coating method as well as deposition, which is economically effective in terms of time and costs.

In addition, when forming a coating layer using a coating composition including the fluorene derivative including a thermo-curable group or a photo-curable group, the thermo-curable group or the photo-curable group forms crosslinkage by heat or light, and therefore, the fluorene derivative included in the coating composition being washed away by a solvent may be prevented when laminating an additional layer on the top of the coating layer, and the additional layer may be laminated while maintaining the coating layer.

Additionally, forming a coating layer by the thermo-curable group or the photo-curable group forming crosslinkage is effective in increasing chemical resistance of the coating layer for a solvent, and obtaining a high film retention rate.

In addition, in the fluorene derivative according to one embodiment of the present specification, an organic light emitting device may be manufactured using a solution coating method, and therefore, large-area devices may be manufactured.

According to one embodiment of the present specification, the fluorene derivative in which crosslinkage is formed by heat treatment or light irradiation is effective in obtaining excellent thermal stability since a plurality of the fluorene derivatives are crosslinked and provided in an organic light emitting device in a thin film form. Accordingly, an organic light emitting device using the fluorene derivative according to one embodiment of the present specification has an excellent life time property.

In addition, the fluorene derivative according to one embodiment of the present specification has an amine structure in the core structure, and therefore, may have proper energy level and band gap as a hole injection material, a hole transfer material or a light emitting material in an organic light emitting device. Furthermore, an organic light emitting device having a low driving voltage and high light emission efficiency may be manufactured by finely adjusting the proper energy level and band gap through controlling substituents of the compound of Chemical Formula 1 according to one embodiment of the present specification, and enhancing interfacial properties between organic materials.

According to one embodiment of the present disclosure, the compound of Chemical Formula 1 is represented by any one of the following structural formulae.

[Chemical Formula 1-1-1]

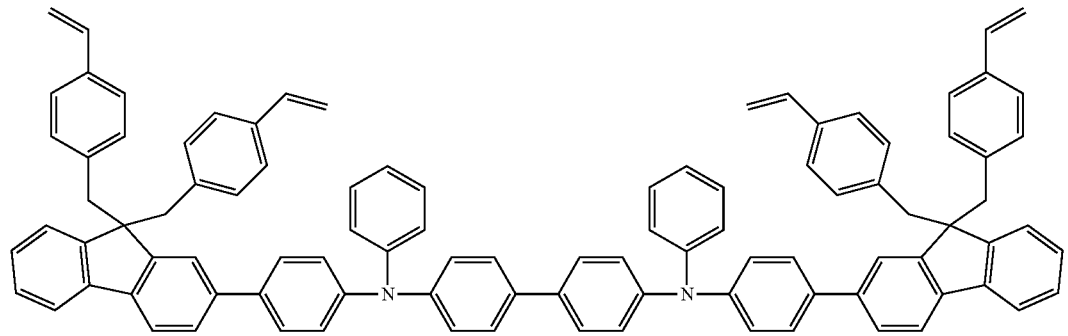

[Chemical Formula 1-1-2]

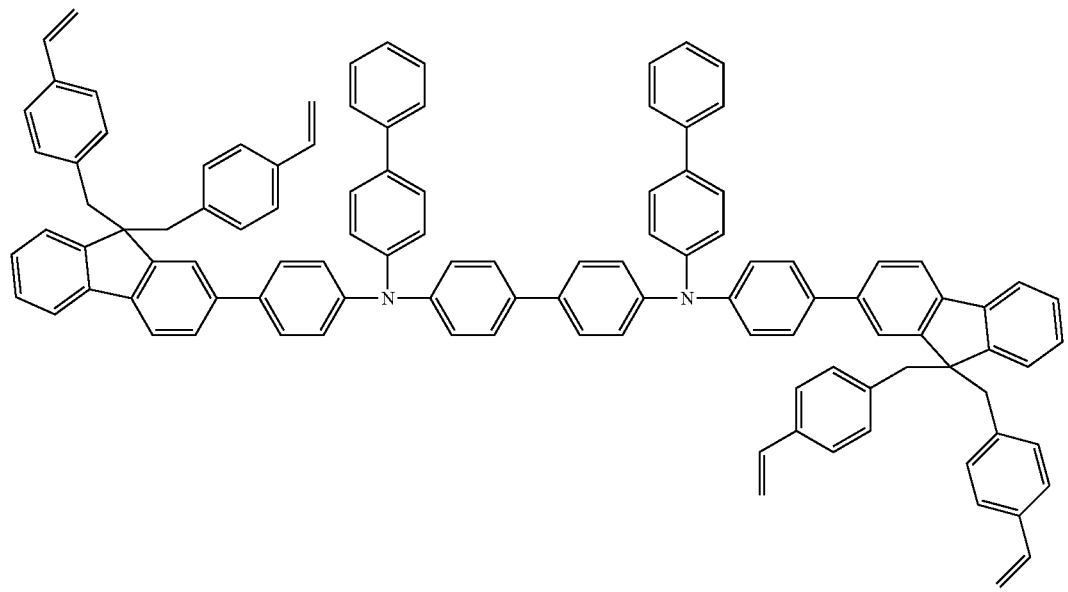

[Chemical Formula 1-1-3]

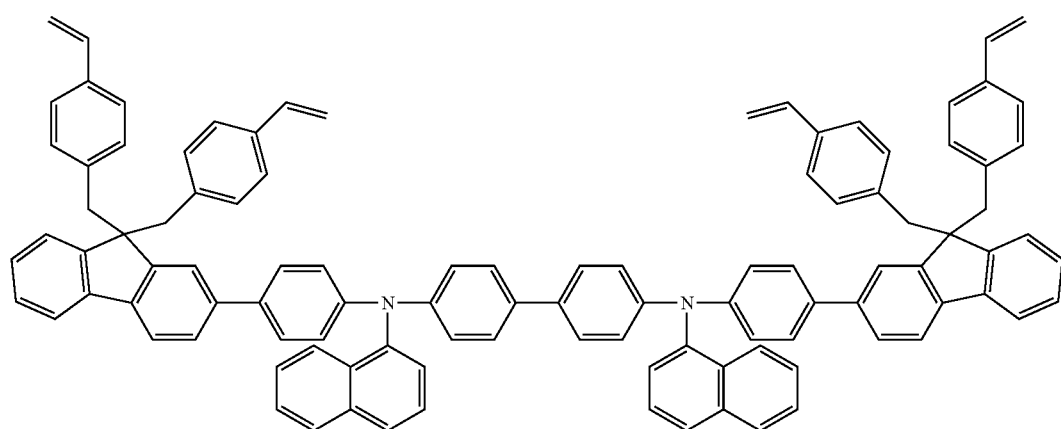

[Chemical Formula 1-1-4]
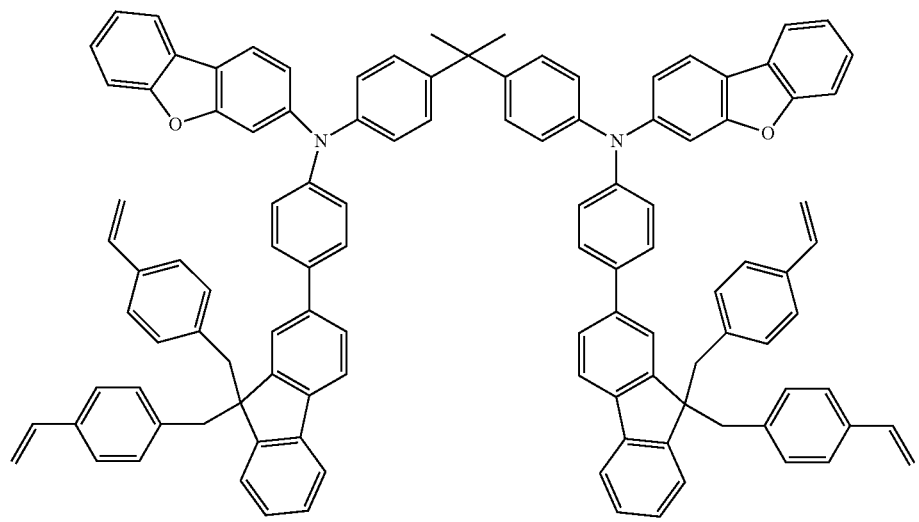
[Chemical Formula 1-1-5]
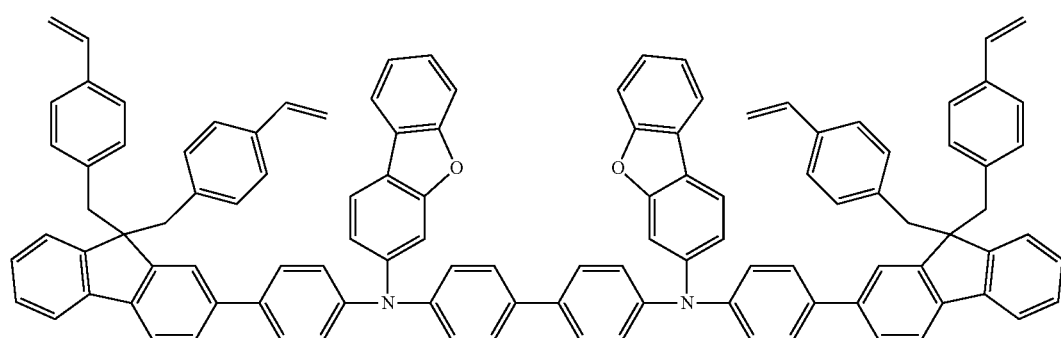
[Chemical Formula 1-1-6]
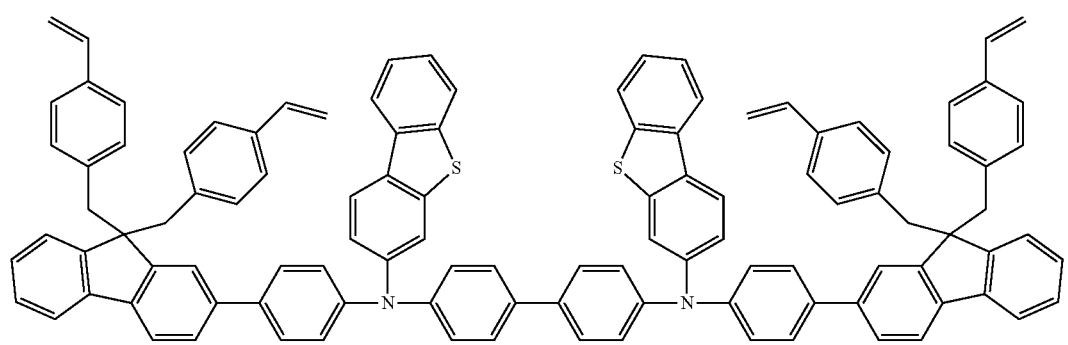
[Chemical Formula 1-1-7]
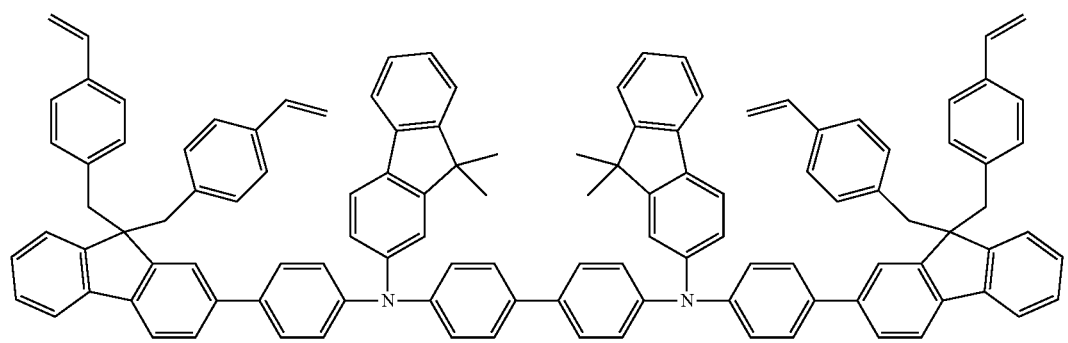

The compound according to one embodiment of the present specification may be prepared using a preparation method to describe later.

Substituents may bond using methods known in the art, and, types, positions or the number of the substituents may vary depending on technologies known in the art.

The present specification also provides a coating composition including the fluorene derivative described above.

In one embodiment of the present specification, the coating composition may be a liquid phase. The "liquid phase" means in a liquid state at room temperature and atmospheric pressure.

In one embodiment of the present specification, the coating composition includes the fluorene derivative and a solvent.

In one embodiment of the present specification, examples of the solvent may include chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone, cyclohexanone, isophorone, tetralone, decalone or acetylacetone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; tetraline, and the like, however, the solvent is not limited as long as it is a solvent capable of dissolving and dispersing the fluorene derivative according to one embodiment of the present disclosure.

In another embodiment, the solvent may be used either alone as one type, or as a mixture mixing two or more solvent types.

In one embodiment of the present specification, the coating composition may further include one or two types of compounds selected from the group consisting of a compound having a thermo-curable group or a photo-curable group introduced into the molecule and a polymer compound.

In one embodiment of the present specification, the coating composition may further include a compound having a thermo-curable group or a photo-curable group introduced into the molecule. When the coating composition further includes a compound having a thermo-curable group or a photo-curable group introduced into the molecule, the degree of curing of the coating composition may be further enhanced.

In one embodiment of the present specification, the compound having a thermo-curable group or a photo-curable group introduced into the molecule has a molecular weight of 100 g/mol to 1,500 g/mol.

In one embodiment of the present specification, the coating composition may further include a polymer compound. When the coating composition further includes a polymer compound, ink properties of the coating composition may be enhanced. In other words, the coating composition further including a polymer compound may provide proper viscosity for coating or inkjet.

In one embodiment of the present specification, the coating composition has viscosity of 2 cP to 15 cP. A device is readily manufactured when having viscosity in the above-mentioned range.

In one embodiment of the present specification, the polymer compound has a molecular weight of 10,000 g/mol to 200,000 g/mol.

In one embodiment of the present specification, the coating composition may further include one, two or more types of additives selected from the group consisting of a thermal polymerization initiator and a photopolymerization initiator.

Examples of the thermal polymerization initiator may include peroxides such as methyl ethyl ketone peroxide, methyl isobutyl ketone peroxide, acetylacetone peroxide, methylcyclohexanone peroxide, cyclohexanone peroxide, isobutyryl peroxide, 2,4-dichlorobenzoyl peroxide, bis-3,5,5-trimethyl hexanoyl peroxide, lauryl peroxide, benzoyl peroxide, p-chlorobenzoyl peroxide, dicumyl peroxide, 2,5-dimethyl-2,5-(t-butyloxy)-hexane, 1,3-bis(t-butylperoxyisopropyl)benzene, t-butyl cumyl peroxide, di-t-butyl peroxide, 2,5-dimethyl-2,5-(di-t-butylperoxy)hexane-3, tris-(t-butylperoxy)triazine, 1,1-di-t-butylperoxy-3,3,5-trimethylcyclohexane, 1,1-di-t-butylperoxycyclohexane, 2,2-di(t-butylperoxy)butane, 4,4-di-t-butylperoxy valeric acid n-butyl ester, 2,2-bis(4,4-t-butylperoxycyclohexyl)propane, t-butyl peroxyisobutyrate, di-t-butyl peroxyhexahydroterephthalate, t-butylperoxy-3,5,5-trimethylhexate, t-butyl peroxybenzoate or di-t-butyl peroxytrimethyl adipate; or azo-based such as azobis isobutylnitrile, azobis dimethylvaleronitrile or azobis cyclohexyl nitrile, but are not limited thereto.

Examples of the photopolymerization initiator may include acetophenone-based or ketal-based photopolymerization initiators such as diethoxyacetophenone, 2,2-dimethoxy-1,2-diphenyl ethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl)propan-1-one or 1-phenyl-1,2-propanedion-2-(o-ethoxycarbonyl)oxime; benzoin ether-based photopolymerization initiators such as benzoin, benzoin methyl ether, benzoin ethyl ether, benzoin isobutyl ether or benzoin isopropyl ether; benzophenone-based photopolymerization initiators such as benzophenone, 4-hydroxybenzophenone, 2-benzoylnaphthalene, 4-benzoylbiphenyl, 4-benzoyl phenyl ether, acrylated benzophenone or 1,4-benzoylbenzene; thioxanthone-based photopolymerization initiators such as 2-isopropylthioxanthone, 2-chlorothioxanthone, 2,4-dimethylthioxanthone, 2,4-diethylthioxanthone or 2,4-dichlorothioxanthone; ethyl anthraquinone; 2,4,6-trimethylbenzoyldiphenylphosphine oxide; 2,4,6-trimethylbenzoylphenylethoxyphosphine oxide; bis(2,4,6-trimethylbenzoyl)phenylphosphine oxide; bis(2,4-dimethoxybenzoyl)-2,4,4-trimethylpentylphosphine oxide; methylphenylglyoxyester; 9,10-phenanthrene; acridine-based compounds; triazine-based compounds; imidazole-based compounds, and the like. In addition, those having a photopolymerization facilitating effect may be used either alone or together with the photopolymerization initiator. Examples thereof may include triethanolamine, methyldiethanolamine, ethyl 4-dimethylaminobenzoate, isoamyl 4-dimethylaminobenzoate, (2-dimethylamino)ethyl benzoate, 4,4'-dimethylaminobenzophenone and the like, but are not limited thereto.

In one embodiment of the present specification, the coating composition does not further include a p-doping material.

In another embodiment, the coating composition further includes a p-doping material.

In the present specification, the p-doping material means a material enabling a host material to have a p semiconductor property. The p semiconductor property means a property receiving holes through injecting or transferring holes at a highest occupied molecular orbital (HOMO) energy level, that is, a property of a material having high hole conductivity.

In one embodiment of the present specification, the p-doping material may be represented by any one of the following structures.

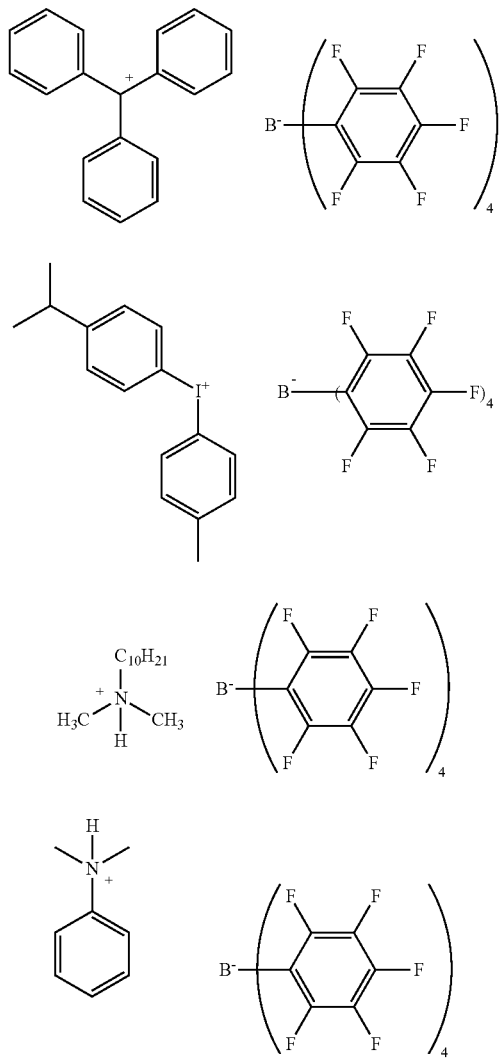

In one embodiment of the present specification, the p-doping material may include an anionic group represented by the following Chemical Formula 2.

[Chemical Formula 2]

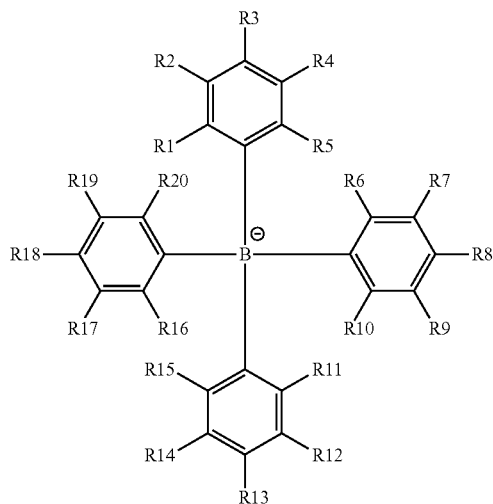

In Chemical Formula 2, at least one of R1 to R20 is F, a cyano group, or a substituted or unsubstituted fluoroalkyl group, at least one of the remaining R1 to R20 is a thermo-curable group or a photo-curable group, the remaining R1 to R20 are the same as or different from each other, and each independently hydrogen; deuterium; a nitro group; —C(O)R$_{100}$; —OR$_{101}$; —SR$_{102}$; —SO$_3$R$_{103}$; —COOR$_{104}$; —OC(O)R$_{105}$; —C(O)NR$_{106}$R$_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group, and R$_{100}$ to R$_{107}$ are the same as or different from each other, and each independently hydrogen; deuterium; or a substituted or unsubstituted alkyl group.

The thermo-curable group or the photo-curable group are selected from among the following structures.

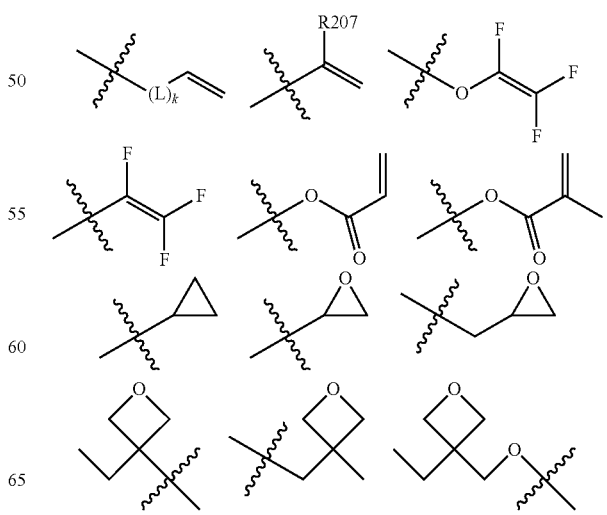

-continued

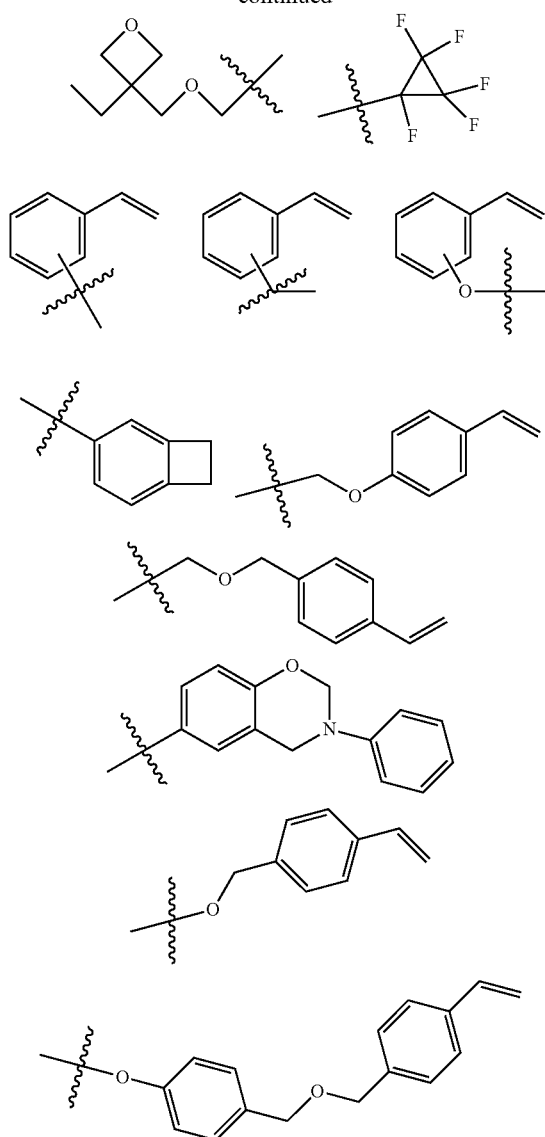

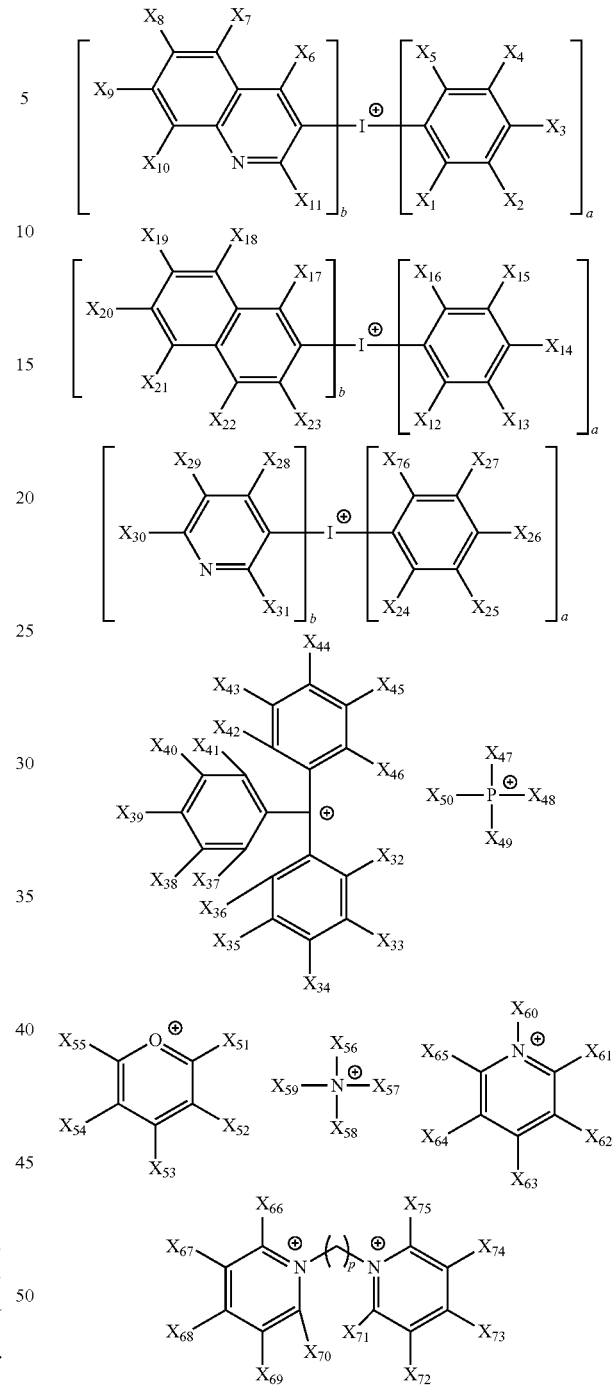

In the structures,

R207 is hydrogen; deuterium; a halogen group; a substituted or unsubstituted alkyl group; a substituted or unsubstituted cycloalkyl group; a substituted or unsubstituted amine group; a substituted or unsubstituted arylamine group; a substituted or unsubstituted silyl group; a substituted or unsubstituted aryl group; or a substituted or unsubstituted heterocyclic group, L is a direct bond; O; S; a substituted or unsubstituted alkylene group; a substituted or unsubstituted arylene group; or a substituted or unsubstituted divalent heterocyclic group, and k is an integer of 1 or 2, and when k is 2, substituents in the parentheses are the same as or different from each other.

In one embodiment of the present specification, the p-doping material may further include a cationic group, and the cationic group may be selected from among monovalent cation groups, onium compounds or the following structural formulae.

In the structural formulae, $X_1$ to $X_{76}$ are the same as or different from each other, and each independently hydrogen; a cyano group; a nitro group; a halogen group; —COOR$_{108}$; a substituted or unsubstituted alkyl group; a substituted or unsubstituted alkoxy group; a substituted or unsubstituted cycloalkyl group; a substituted or unsubstituted fluoroalkyl group; or a substituted or unsubstituted aryl group, or a thermo-curable group or a photo-curable group, $R_{108}$ is hydrogen; deuterium; or a substituted or unsubstituted alkyl group, p is an integer of 0 to 10, and a is 1 or 2, b is 0 or 1, and a+b=2.

The p-doping material according to one embodiment of the present specification includes a functional group polymerized by heat or light, and therefore, when providing sufficient heat or light after forming a film, resistance for process solvents is formed, and therefore, the p-doping material may contribute to manufacturing an organic light emitting device with no changes in the film properties and having reproducibility.

In one embodiment of the present specification, the p-doping material is selected from among the following structural formulae.

[Chemical Formula 2-1-1]

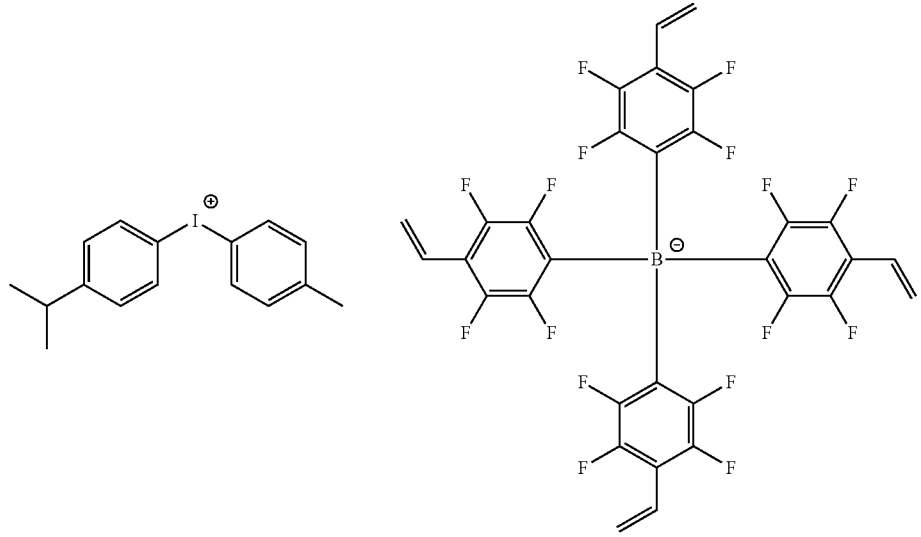

[Chemical Formula 2-1-2]

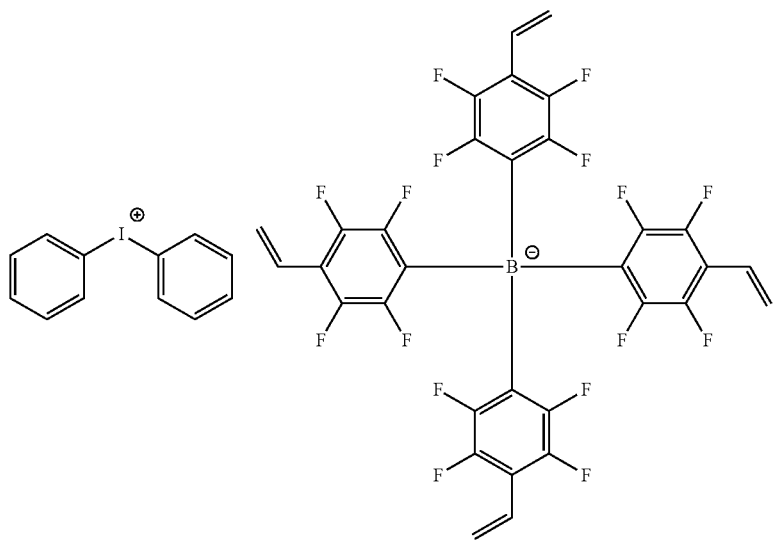

[Chemical Formula 2-1-3]
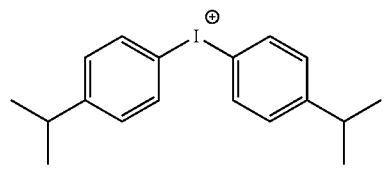 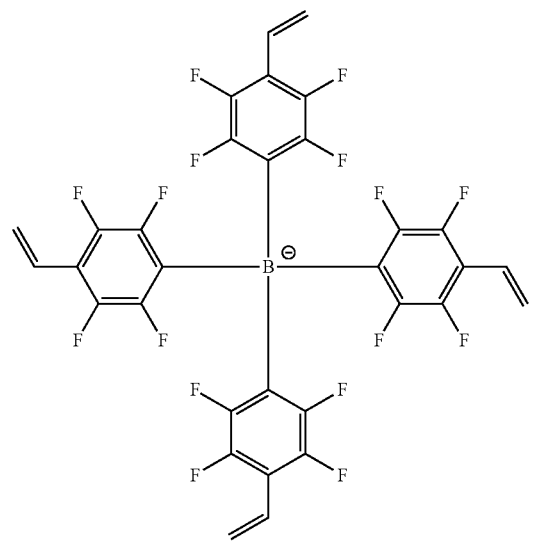
[Chemical Formula 2-1-4]
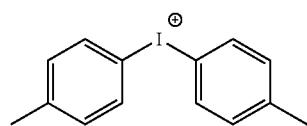 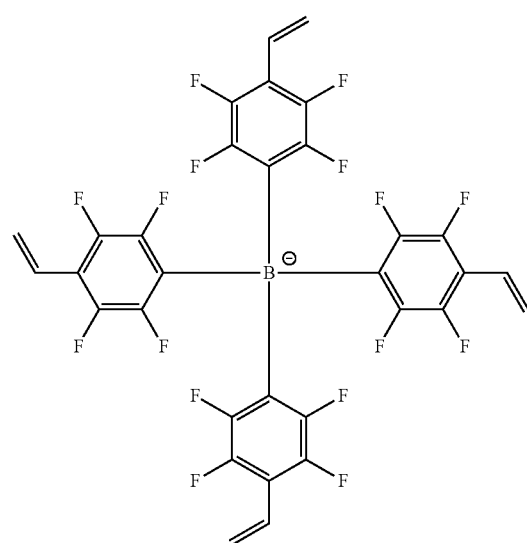
[Chemical Formula 2-1-5]
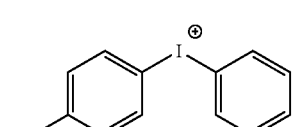 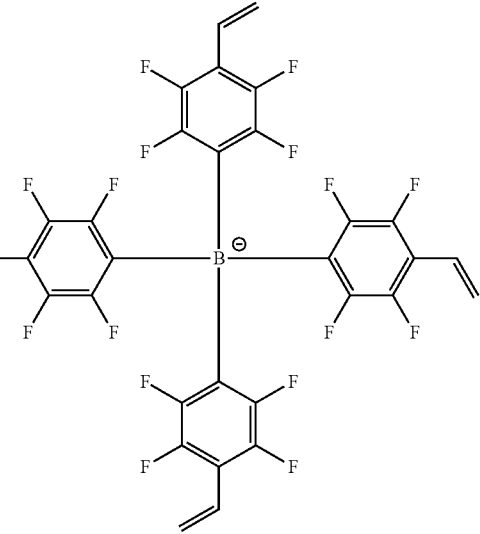

[Chemical Formula 2-1-6]
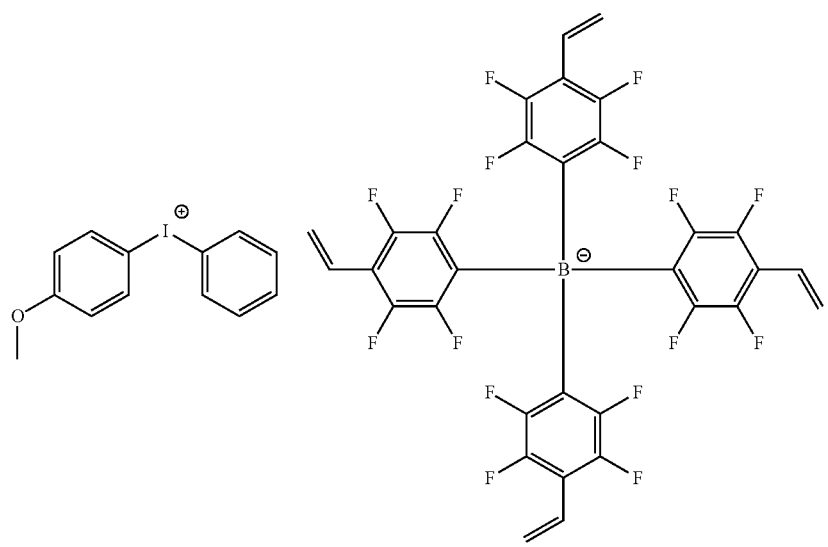
[Chemical Formula 2-1-7]
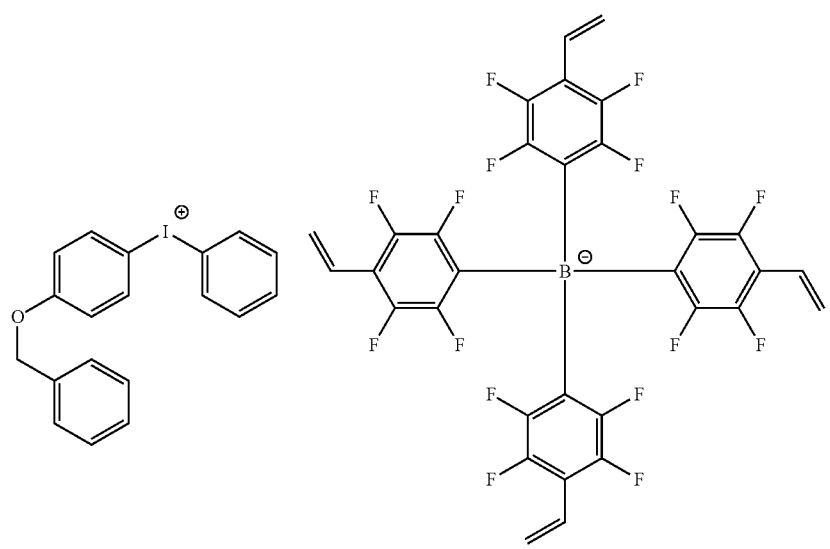
[Chemical Formula 2-1-8]
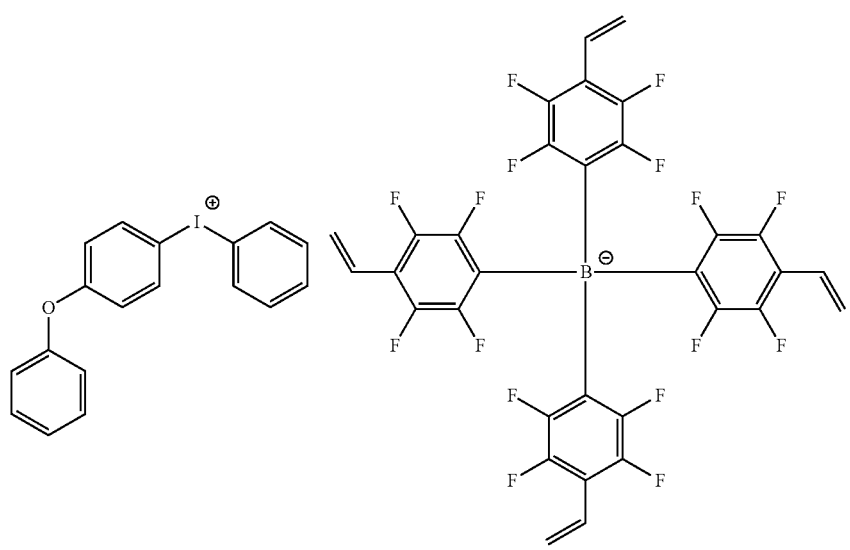

-continued
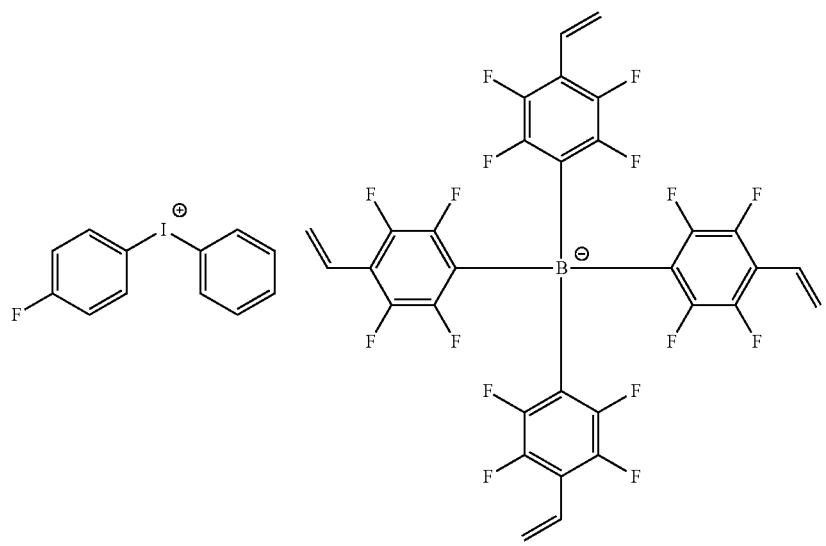
[Chemical Formula 2-1-9]
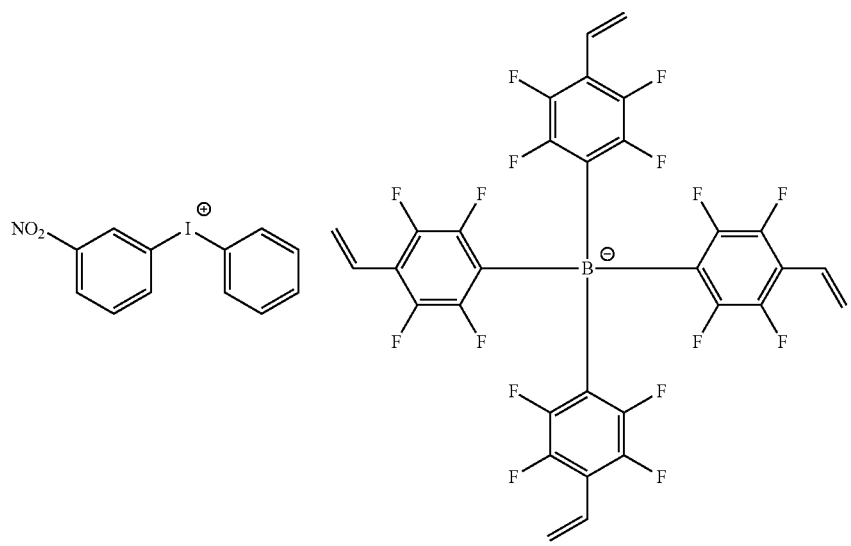
[Chemical Formula 2-1-10]
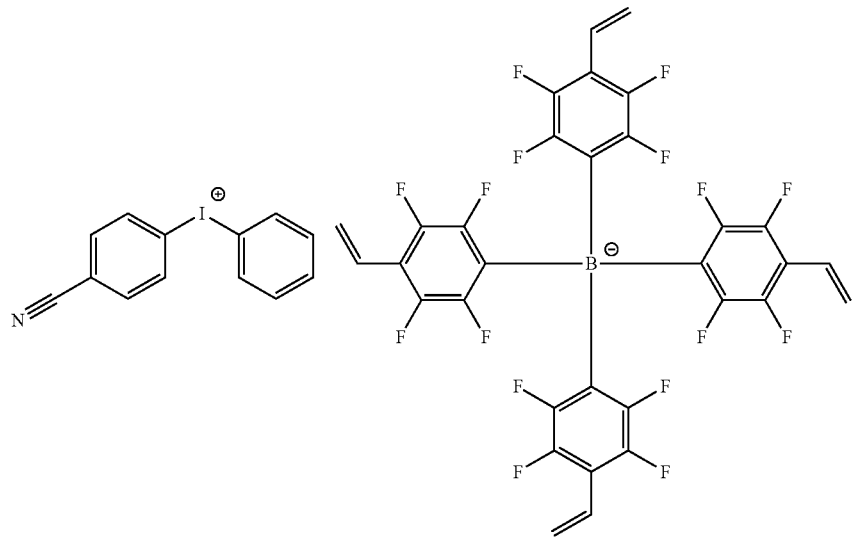
[Chemical Formula 2-1-11]

[Chemical Formula 2-1-12]
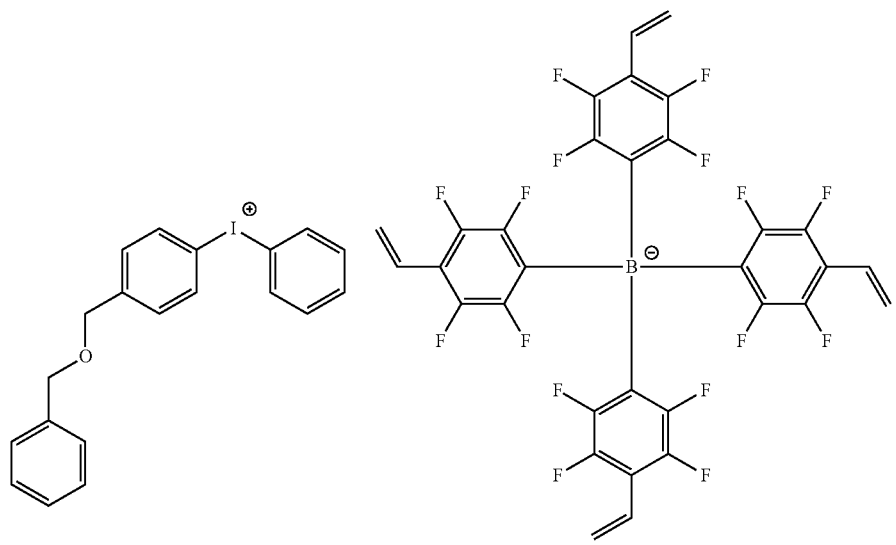
[Chemical Formula 2-1-13]
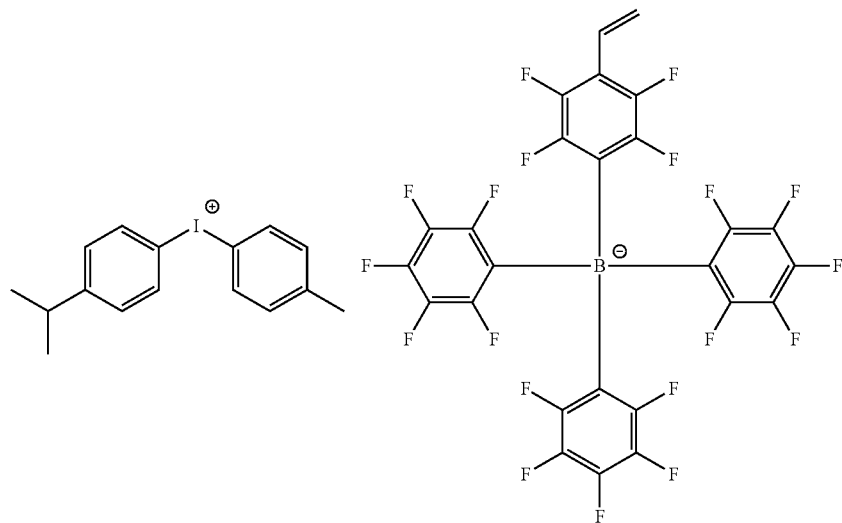
[Chemical Formula 2-1-14]
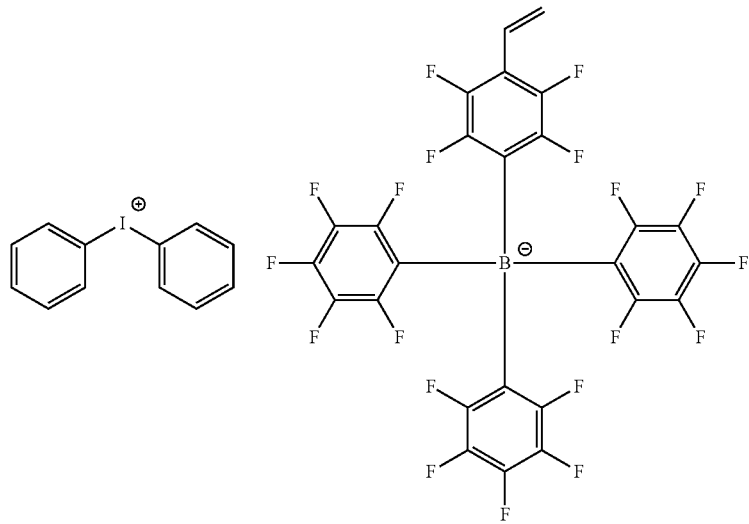

-continued
[Chemical Formula 2-1-15]
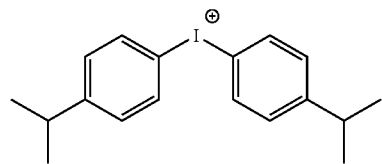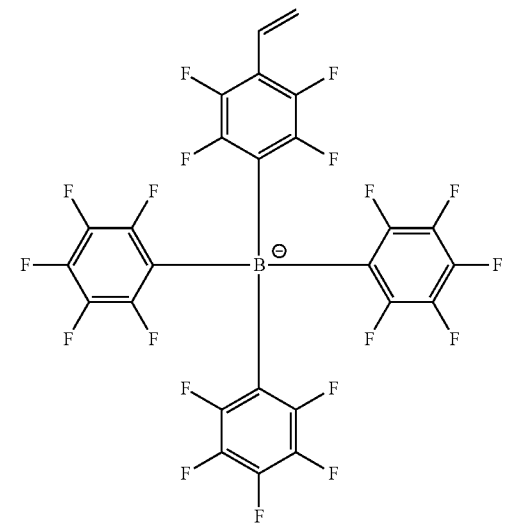
[Chemical Formula 2-1-16]
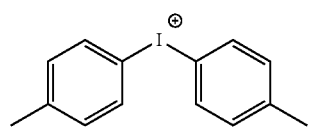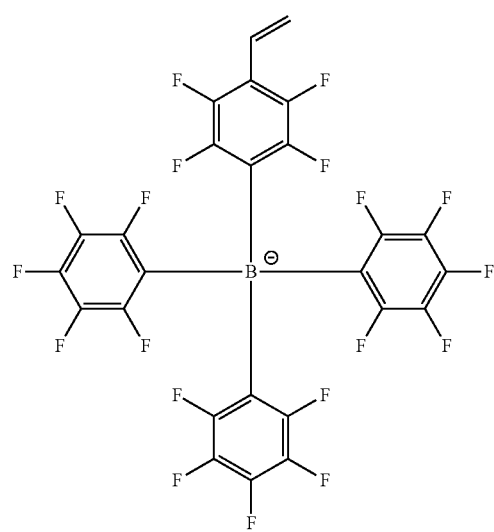
[Chemical Formula 2-1-17]
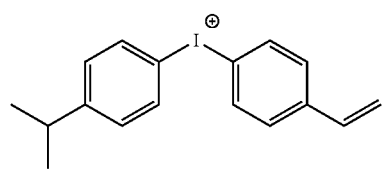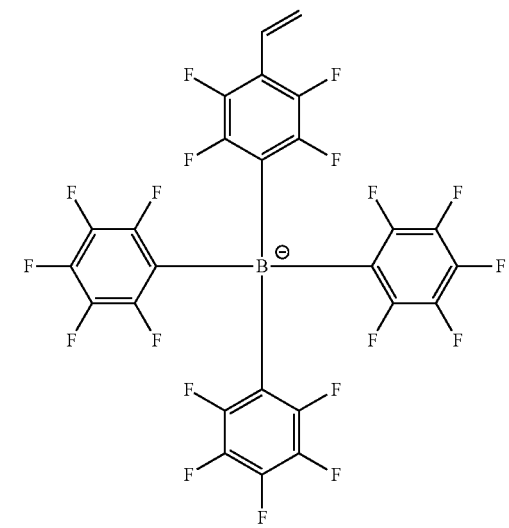

-continued
[Chemical Formula 2-1-18]
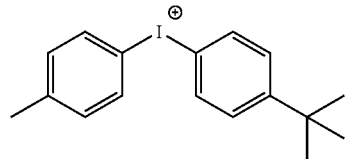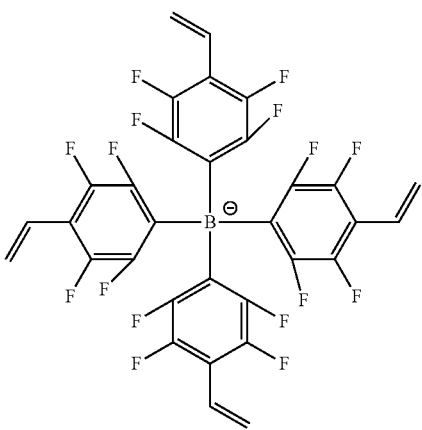
[Chemical Formula 2-1-19]
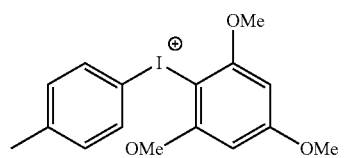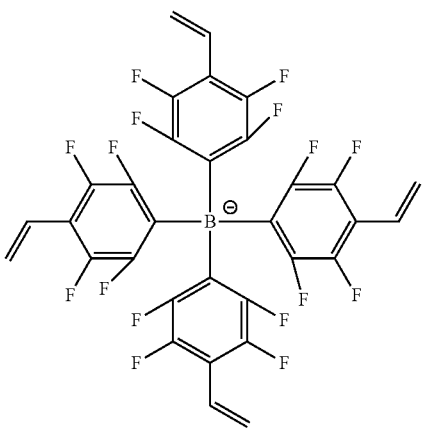
[Chemical Formula 2-1-20]
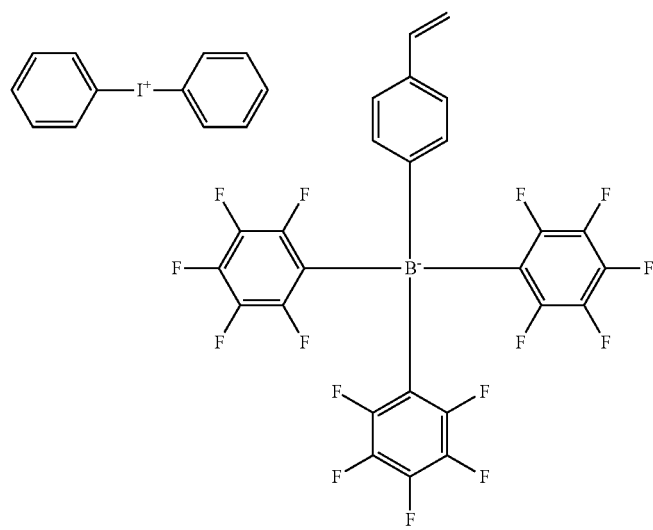

[Chemical Formula 2-1-21]
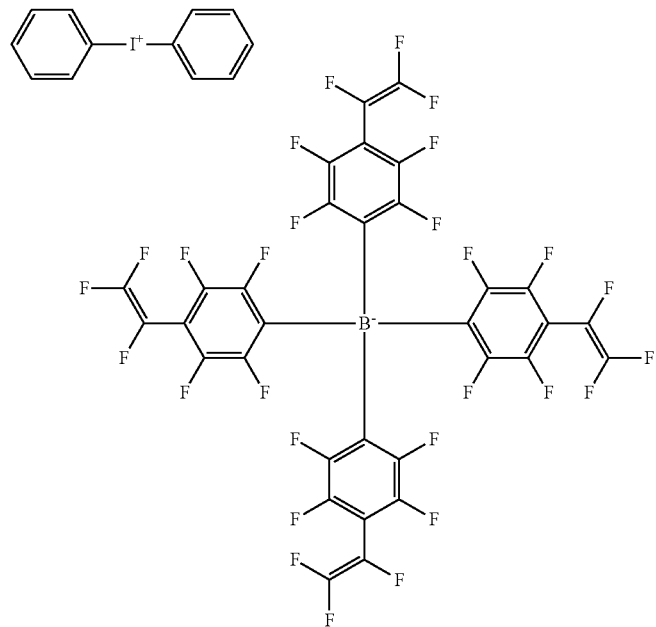
[Chemical Formula 2-1-22]
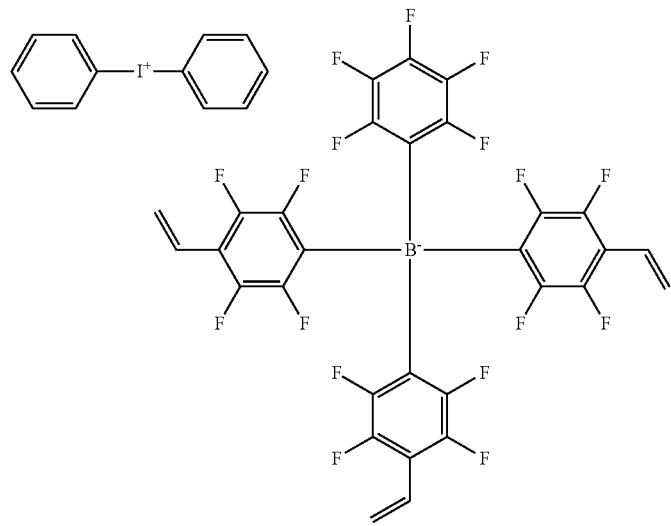

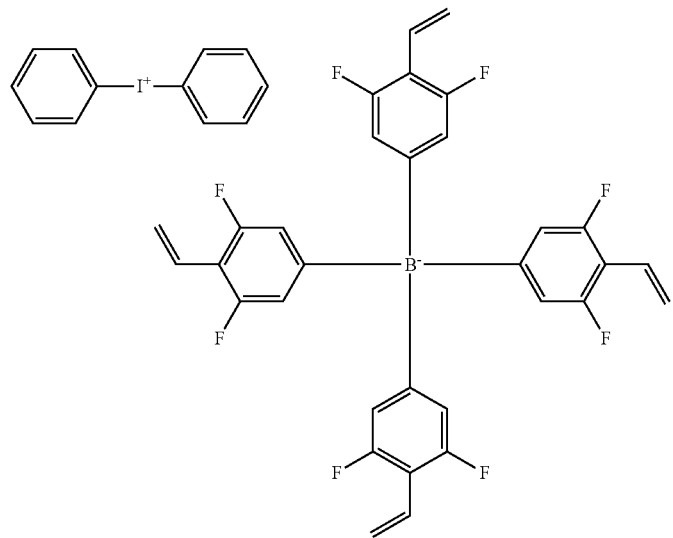
[Chemical Formula 2-1-23]
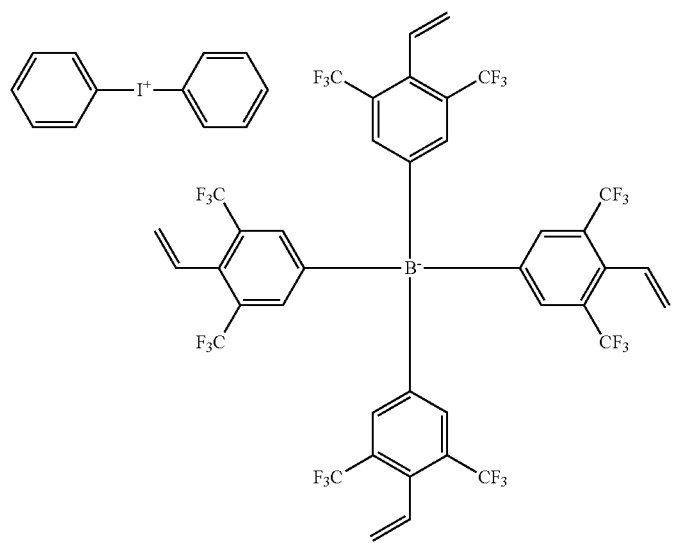
[Chemical Formula 2-1-24]

-continued

[Chemical Formula 2-1-25]

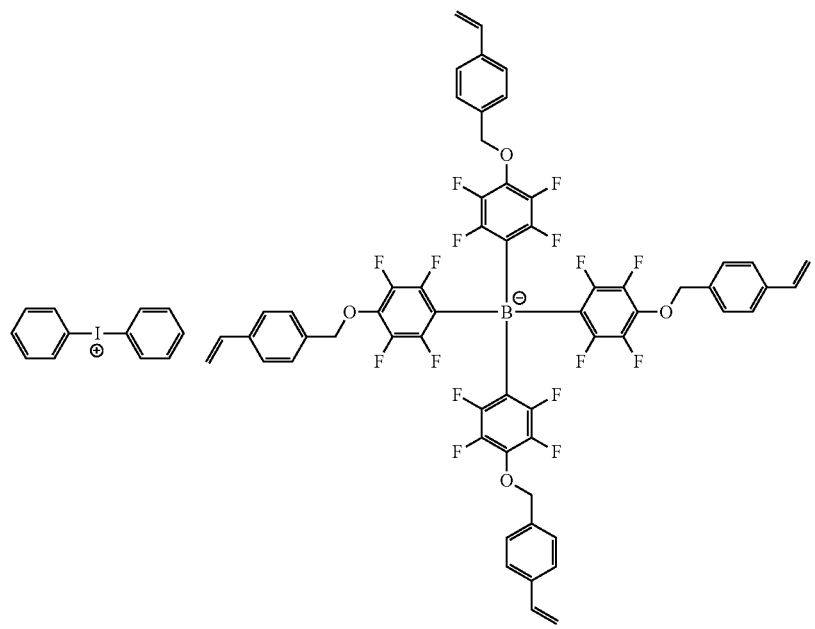

[Chemical Formula 2-1-26]

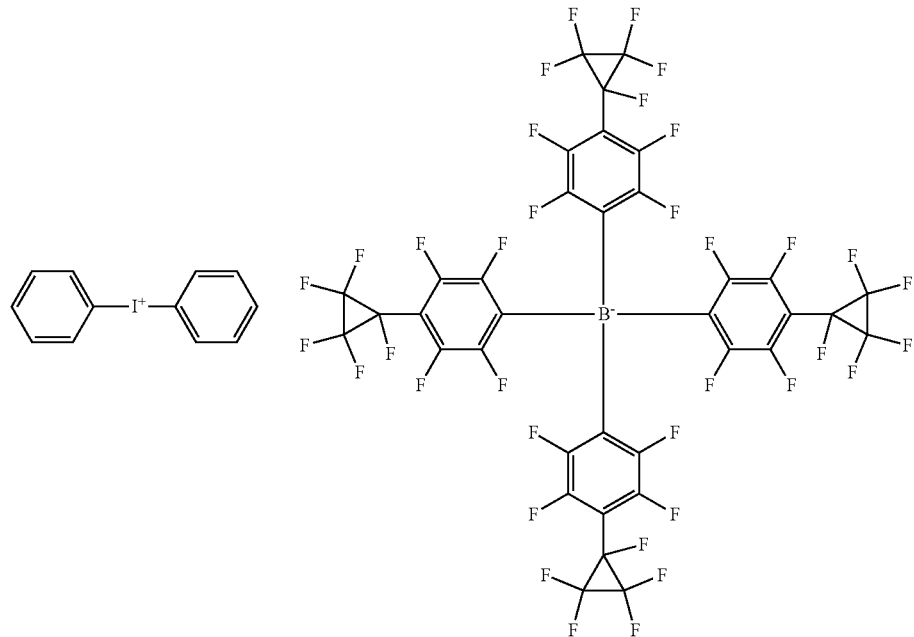

In one embodiment of the present specification, a content of the p-doping material is from 0% by weight to 50% by weight based on the fluorene derivative of Chemical Formula 1.

In one embodiment of the present specification, a content of the p-doping material is from 0% by weight to 30% by weight based on a total solid content of the coating composition.

In one embodiment of the present specification, a content of the p-doping material is preferably from 1% by weight to 30% by weight based on a total solid content of the coating composition, and in another embodiment, a content of the p-doping material is more preferably from 10% by weight to 30% by weight based on a total solid content of the coating composition.

In another embodiment, the coating composition may further include a monomer including a thermo-curable group or a photo-curable group; or a monomer including an end group capable of forming a polymer by heat. The monomer including a thermo-curable group or a photo-curable group; or the monomer including an end group capable of forming a polymer by heat as above may be a compound having a molecular weight of 2,000 g/mol or less.

As in one embodiment of the present specification, the coating composition further including a monomer including a thermo-curable group or a photo-curable group; or a monomer including an end group capable of forming a polymer by heat may lower a curing temperature, and is preferably formed with similar structures having no influences on properties of the fluorene derivative of the present specification.

The monomer including a thermo-curable group or a photo-curable group; or the monomer including an end group capable of forming a polymer by heat may mean aryl such as phenyl, biphenyl, fluorene and naphthalene; arylamine; or a monomer in which fluorene is substituted with a thermo-curable group, a photo-curable group or an end group capable of forming a polymer by heat.

The present specification also provides an organic light emitting device formed using the coating composition.

One embodiment of the present specification provides an organic light emitting device including a cathode; an anode; and one or more organic material layers provided between the cathode and the anode, wherein one or more layers of the organic material layers include a cured material of the coating composition described above, and the cured material of the coating composition is in a cured state by heat treatment or light treatment on the coating composition.

In one embodiment of the present specification, the organic material layer including the cured material of the coating composition is a hole transfer layer, a hole injection layer, or a layer carrying out hole transfer and hole injection at the same time.

In another embodiment, the organic material layer including the cured material of the coating composition is a light emitting layer.

In another embodiment, the organic material layer including the cured material of the coating composition is a light emitting layer, and the light emitting layer includes the fluorene derivative as a host of the light emitting layer.

In one embodiment of the present specification, the organic light emitting device further includes one, two or more layers selected from the group consisting of a hole injection layer, a hole transfer layer, an electron transfer layer, an electron injection layer, an electron blocking layer and a hole blocking layer.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may be formed in a multilayer structure in which two or more organic material layers are laminated. For example, the organic light emitting device of the present specification may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

For example, a structure of the organic light emitting device according to one embodiment of the present specification is illustrated in FIG. 1.

FIG. 1 illustrates a structure of the organic light emitting device in which an anode (201), a hole injection layer (301), a hole transfer layer (401), a light emitting layer (501), an electron transfer layer (601) and a cathode (701) are consecutively laminated on a substrate (101).

In FIG. 1, the hole injection layer (301) is formed using the coating composition including the fluorene derivative.

FIG. 1 illustrates the organic light emitting device, and the structure is not limited thereto.

When the organic light emitting device includes a plurality of organic material layers, the organic material layers may be formed with materials that are the same as or different from each other.

The organic light emitting device of the present specification may be manufactured using materials and methods known in the art, except that one or more layers of the organic material layers are formed using the coating composition including the fluorene derivative.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

One embodiment of the present specification provides a method for manufacturing an organic light emitting device formed using the coating composition.

Specifically, the method for preparing an organic light emitting device includes preparing a substrate; forming a cathode or an anode on the substrate; forming one or more organic material layers on the cathode or the anode; and forming an anode or a cathode on the organic material layers, wherein the forming of an organic material layer uses the coating composition.

In one embodiment of the present specification, the cathode or the anode formed on the substrate, and the anode or the cathode formed on the organic material layer are different from each other. For example, when the cathode is formed on the substrate, the anode is formed on the organic material layer.

In one embodiment of the present specification, the organic material layer formed using the coating composition is formed using spin coating.

In another embodiment, the organic material layer formed using the coating composition is formed using inkjet printing.

In another embodiment, the organic material layer formed using the coating composition is formed using a printing method.

In an embodiment of the present specification, examples of the printing method include a nozzle printing method, an offset printing method, a transfer printing method, a screen printing method or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the forming of one or more organic material layers using the coating composition includes coating the coating composition on the cathode or the anode; and heat treating or light treating the coated coating composition.

In one embodiment of the present specification, a heat treatment temperature in the heat treatment is from 85° C. to 300° C.

In another embodiment, a heat treatment time in the heat treatment may be from 1 minute to 1 hour.

In one embodiment of the present specification, when the coating composition does not include additives, crosslinkage is preferably progressed through heat treatment at a temperature of 100° C. to 300° C., and crosslinkage is more preferably progressed at a temperature of 150° C. to 250° C.

In addition, the coating composition of the present specification may further include an initiator, but it is more preferable not to use an initiator.

When the heat treatment or the light treatment is included in the forming of organic material layers formed using the coating composition, an organic material layer including a thin-filmed structure by a plurality of the fluorene derivatives included in the coating composition forming crosslinkage may be provided. In this case, the organic material layer formed using the coating composition may be prevented from being dissolved by a solvent coated on the surface, or being morphologically affected or decomposed.

Accordingly, when an organic material layer formed using the coating composition is formed including the heat treatment or the light treatment, resistance for the solvent increases, and multiple layers may be formed by repeatedly carrying out solution deposition and crosslinking methods, and as a result, a life time property of a device may be enhanced by increasing stability.

In one embodiment of the present specification, the coating composition including the fluorene derivative may use a coating composition mixed and dispersed to a polymer bonding agent.

As the polymer bonding agent in one embodiment of the present specification, those that do not extremely inhibit charge transfer are preferred, and those that do not exhibit strong absorption for visible light are preferably used. Examples of the polymer bonding agent include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

By the fluorene derivative according to one embodiment of the present specification including fluorene and amine group, the fluorene derivative may be included alone in the organic material layer, or the coating composition including the fluorene derivative may be progressed to a thin film through heat treatment or light treatment, or may be included as a copolymer using a coating composition mixed with other monomers. In addition, the coating composition may be included as a copolymer or included as a mixture by using a coating composition mixed with other polymers.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole series compounds; dimerized styryl compounds; BAlq; 10-hydroxybenzo quinoline-metal compounds; benzoxazole, benzthiazole and benzimidazole series compounds; poly(p-phenylenevinylene) (PPV) series polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, but the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including Alq$_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis (10-hydroxybenzo[h]quinolinato) zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, bathocuproine (BCP), aluminum complexes and the like are included, however, the material is not limited thereto.

The organic light emitting device according to the present specification may be a top-emission type, a bottom-emission type or a dual-emission type depending on the materials used.

In one embodiment of the present specification, the coating composition may be included in organic solar cells or organic transistors in addition to organic light emitting devices.

Hereinafter, the present specification will be described in detail with reference to examples. However, the examples according to the present specification may be modified to various different forms, and the scope of the present specification is not to be construed as being limited to the examples described below. Examples of the present specification are provided in order to more fully describe the present specification to those having average knowledge in the art.

Preparation Example

Preparation Example 1. Preparation of Chemical Formula 1-1-1

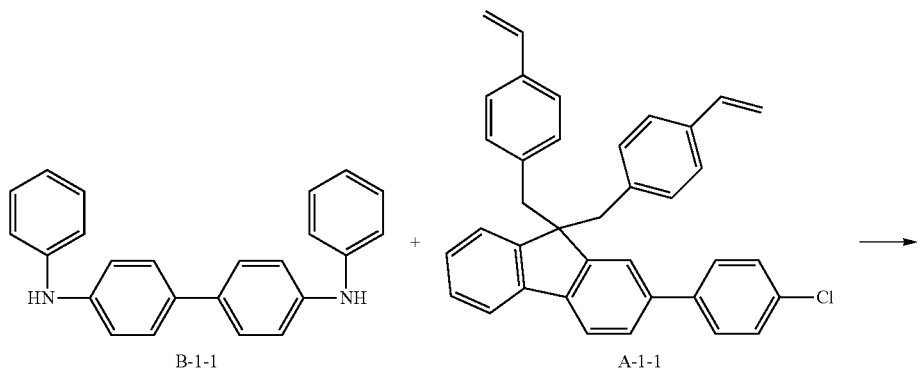

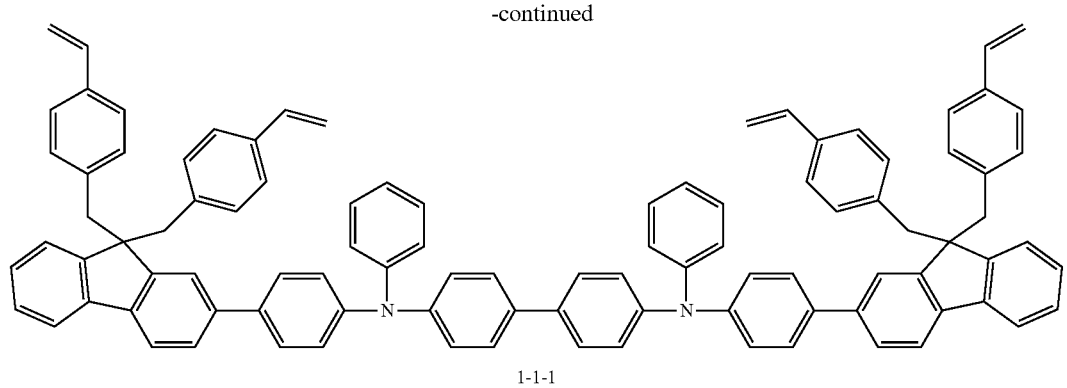

1-1-1

Starting Material B-1-1 (0.5 g, 1.486 mmol), Intermediate A-1-1 (1.59 g, 3.120 mmol), Na(t-BuO) (7.430 mmol) and Pd(t-Bu₃P)₂ (0.051 mmol) were introduced to 50 mL of toluene, the result was reacted for 16 hours at 100° C., and the temperature was lowered to room temperature. After that, the result was dissolved in methylene chloride, then washed with H₂O, and residual water was removed using MgSO₄. After that, the material was purified using column chromatography (ethyl acetate (EA):hexane (Hex)=1:10). (MS: [M+H]+=1281)

Preparation Example 2. Preparation of Chemical Formula 1-1-2

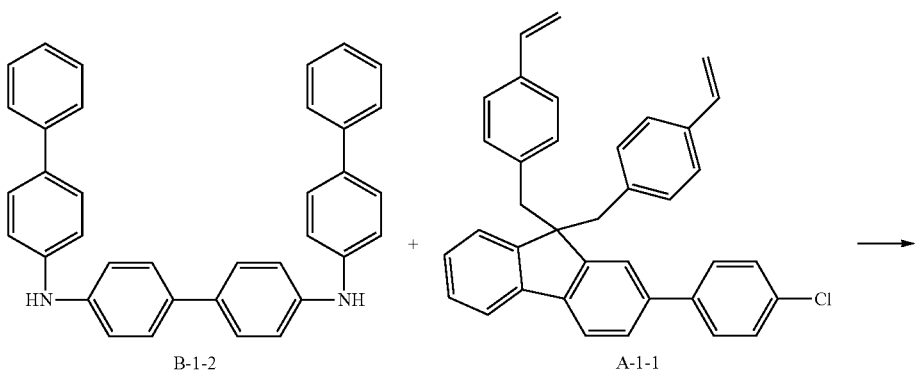

B-1-2 + A-1-1 →

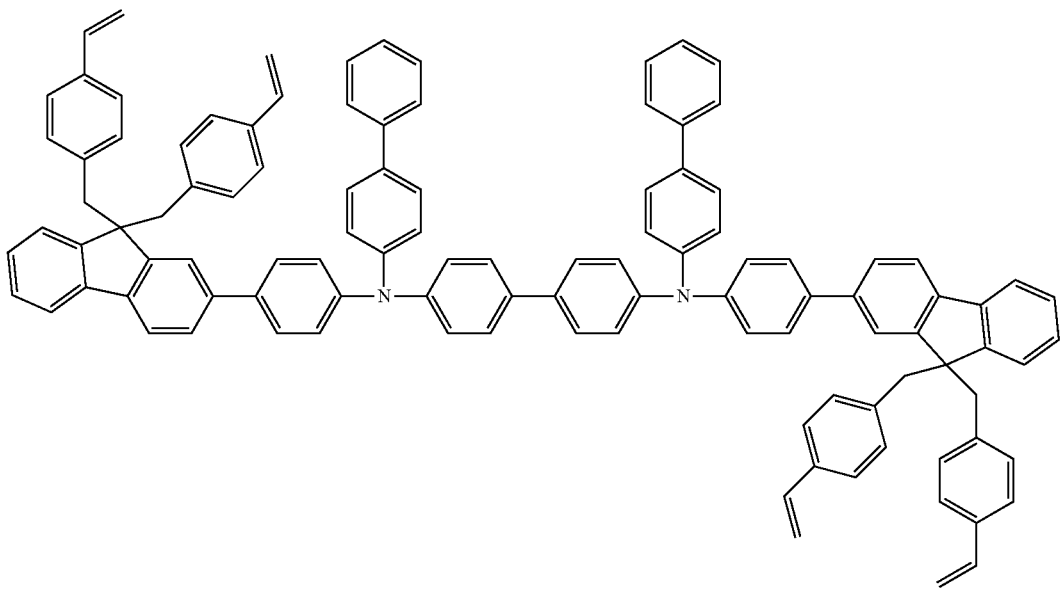

1-1-2

Starting Material B-1-2 (0.5 g, 1.023 mmol), Intermediate A-1-1 (1.09 g, 2.148 mmol), Na(t-BuO)(491 mg, 5.115 mmol) and Pd(t-Bu$_3$P)$_2$ (0.051 mmol) were introduced to 50 mL of toluene, the result was reacted for 16 hours at 100° C., and the temperature was lowered to room temperature. After that, the result was dissolved in methylene chloride, then washed with H$_2$O, and residual water was removed using MgSO$_4$. After that, the material was purified using column chromatography (EA:Hex=1:4). (MS: [M+H]+=1433)

Preparation Example 3. Preparation of Chemical Formula 1-1-3

The following Chemical Formula 1-1-3 was prepared in the same manner as in Preparation Example 1 except that the starting material was changed to the following Chemical Formula B-1-3. (MS: [M+H]+=1383)

B-1-3

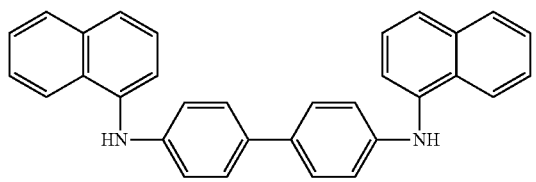

1-1-3

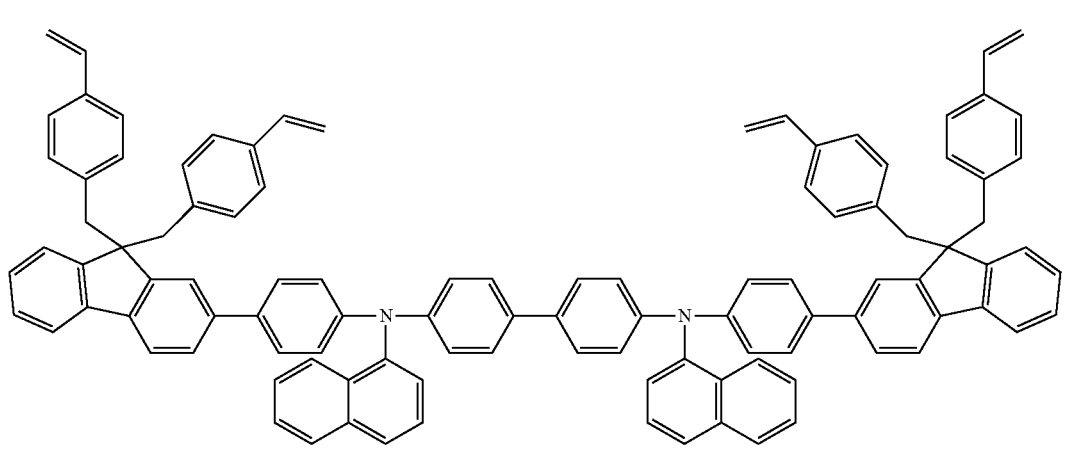

Preparation Example 4. Preparation of Chemical Formula 1-1-4

The following Chemical Formula 1-1-4 was prepared in the same manner as in Preparation Example 1 except that the starting material was changed to the following Chemical Formula B-1-4. (MS: [M+H]+=1503)

B-1-4

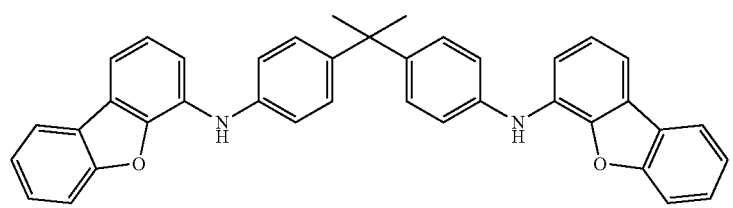

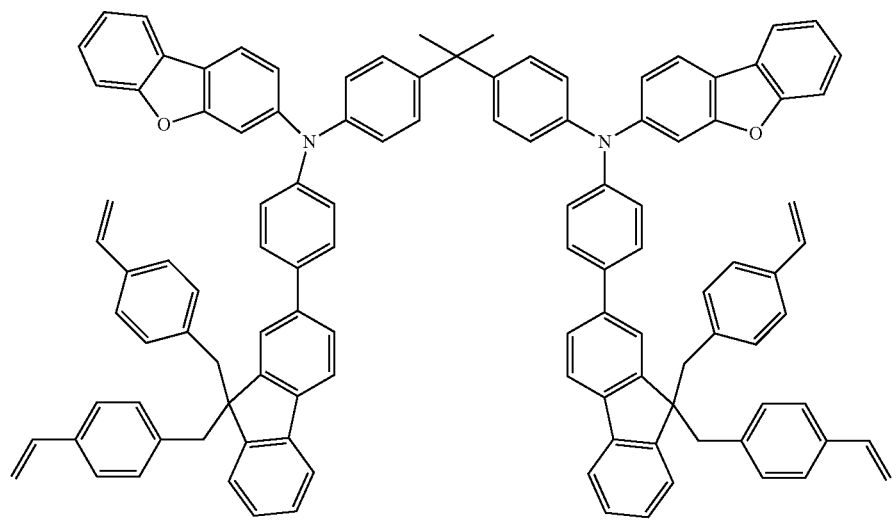

1-1-4

Preparation Example 5. Preparation of Chemical Formula 1-1-5

The following Chemical Formula 1-1-5 was prepared in the same manner as in Preparation Example 1 except that the starting material was changed to the following Chemical Formula B-1-5. (MS: [M+H]+=1461)

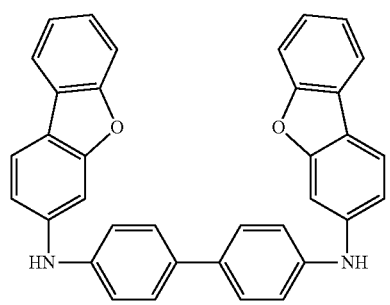

B-1-5

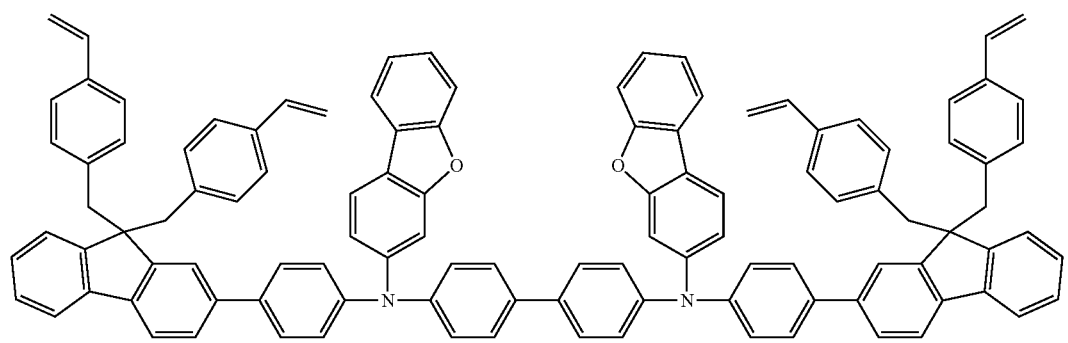

1-1-5

Preparation Example 6. Preparation of Chemical Formula 1-1-6

The following Chemical Formula 1-1-6 was prepared in the same manner as in Preparation Example 1 except that the starting material was changed to the following Chemical Formula B-1-6. (MS: [M+H]$^+$=1493)

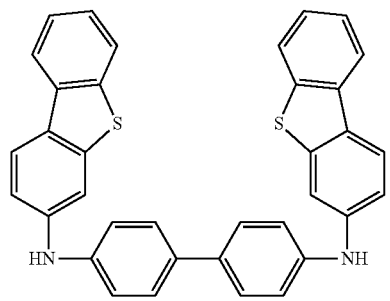
B-1-6
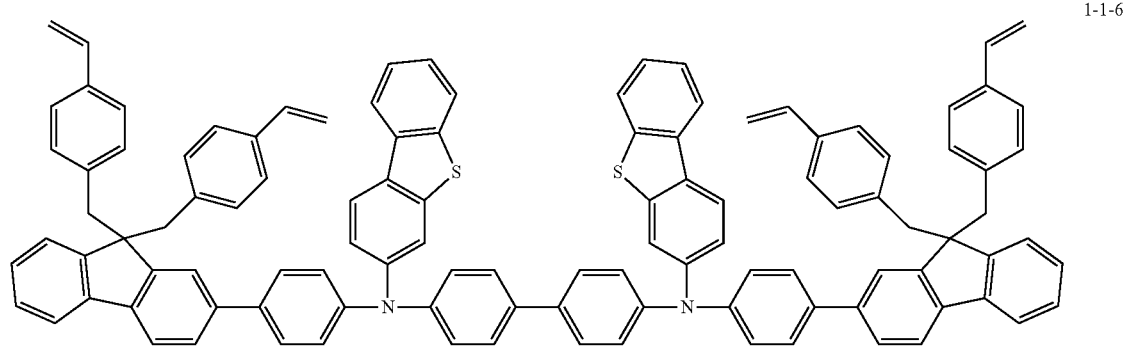
1-1-6
Preparation Example 7. Preparation of Chemical Formula 1-1-7
The following Chemical Formula 1-1-7 was prepared in the same manner as in Preparation Example 1 except that the starting material was changed to the following Chemical Formula B-1-7. (MS: [M+H]+=1513)
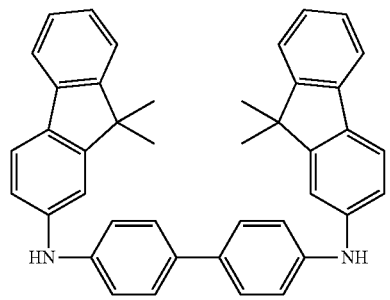
B-1-7
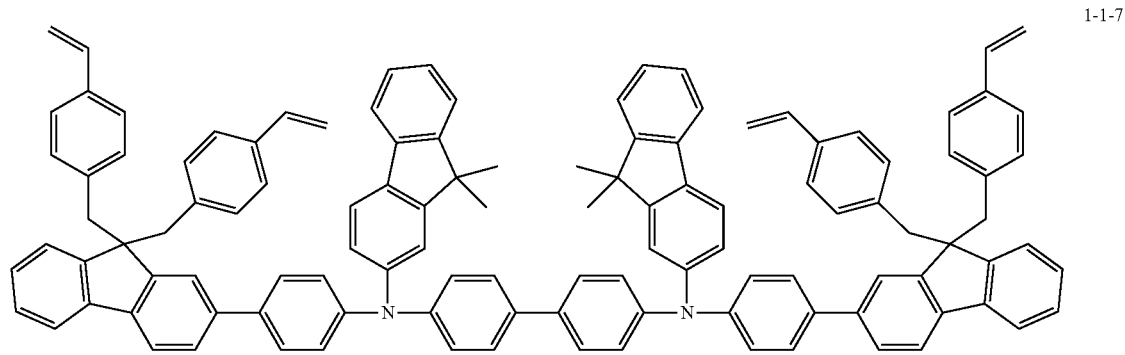
1-1-7

Preparation Example 8. Preparation of Chemical Formula 2-1

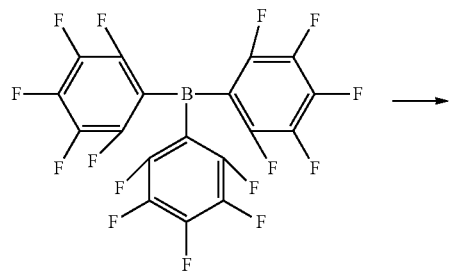

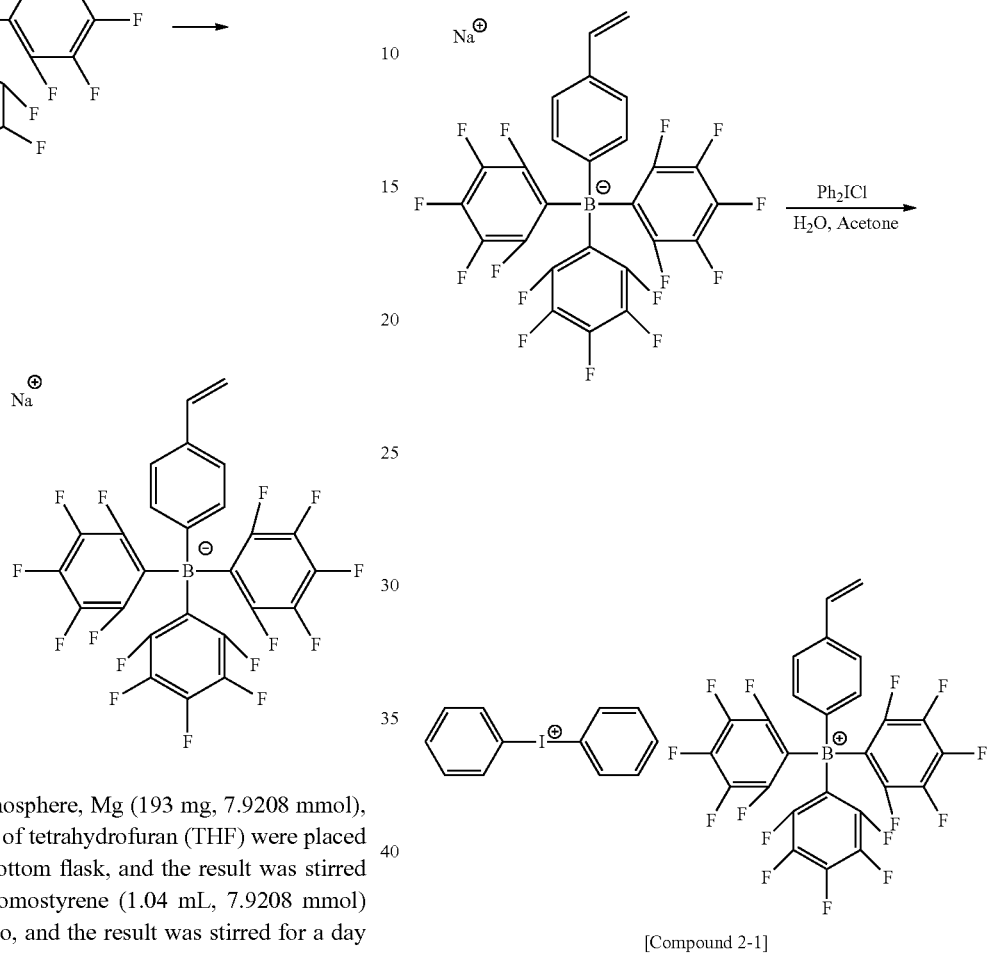

[Compound 2-1]

Under nitrogen atmosphere, Mg (193 mg, 7.9208 mmol), 4 mg of $I_2$ and 10 mL of tetrahydrofuran (THF) were placed in a 100 mL round bottom flask, and the result was stirred for 30 minutes. 4-Bromostyrene (1.04 mL, 7.9208 mmol) was introduced thereto, and the result was stirred for a day while placing a 30° C. water bath under the round bottom flask. After verifying that Mg was dissolved therein as the reaction solution became black, 5 mL of ether was added thereto to dilute the reaction solution. Next, tris(pentafluorophenyl)borane (1 g, 3.9604 mmol) dissolved in 5 mL of ether was slowly added to the reaction solution over 30 minutes. After that, the solution was stirred for a day, and then $Na_2CO_3$ (0.1 M, 80 mL, 8.0 mmol) was slowly added to the reaction solution. After that, the organic solvent was extracted using ethyl acetate (EA) (20 mL×3), and residual water was removed with $MgSO_4$. In order to additionally remove residual water and impurities, the result was distilled with benzene using a Dean-stark. When approximately 10 mL of the solvent remained, the solution was cooled and filtered to obtain 1.6 g of a target compound (sodium tris(perfluorophenyl)(4-vinylphenyl)borate). (Yield: 64%)

Sodium tris(perfluorophenyl)(4-vinylphenyl)borate (100 mg, 0.1567 mmol), 10 mL of distilled water and $Ph_2ICl$ (60 mg, 0.1881 mmol) were placed in a 25 mL a round bottom flask, and the result was stirred for 1 hour. When adding 15 mL of acetone to the reaction solution, precipitates were produced, and these precipitates were filtered and dried to obtain 140 mg of Compound 2-1. (Yield: 100%)

Comparative Preparation Example 1. Preparation of Chemical Formula 1-1

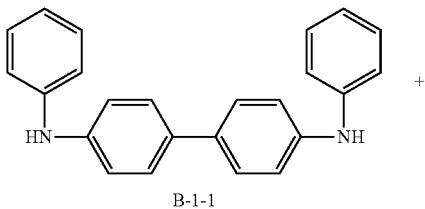

B-1-1

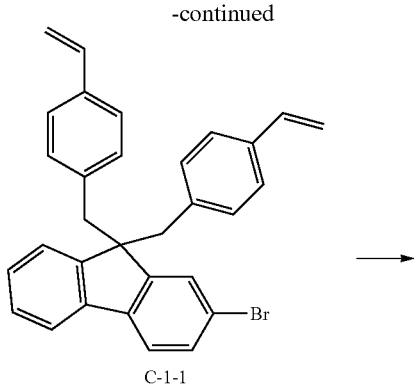

C-1-1

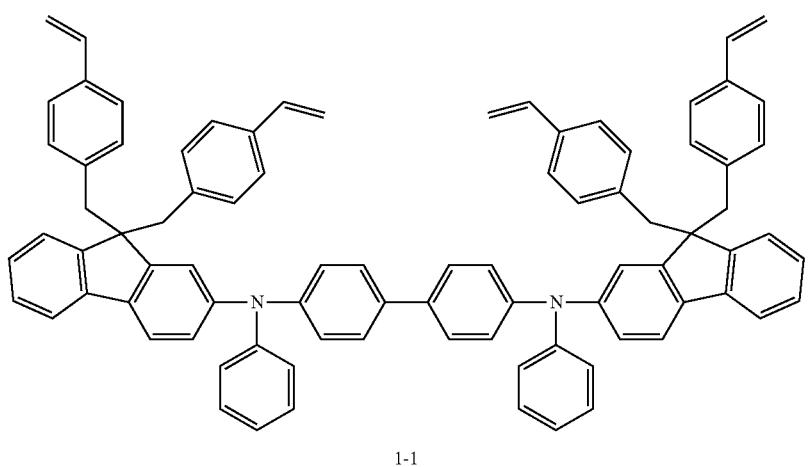

1-1

Starting Material B-1-1 (0.5 g, 1.486 mmol), Intermediate C-1-1 (1.49 g, 3.120 mmol), Na(t-BuO) (7.430 mmol) and Pd(t-Bu$_3$P)$_2$ (0.051 mmol) were introduced to 50 mL of toluene, the result was reacted for 16 hours at 100° C., and the temperature was lowered to room temperature. After that, the result was dissolved in methylene chloride, then washed with H$_2$O, and residual water was removed using MgSO$_4$. After that, the material was purified using column chromatography (EA:Hex=1:25).

Comparative Preparation Example 2. Preparation of Chemical Formula 1-2

The following Chemical Formula 1-2 was prepared in the same manner as in Preparation Example 1 except that the following Chemical Formula A-1-2 was used instead of Chemical Formula A-1-1.

A-1-2

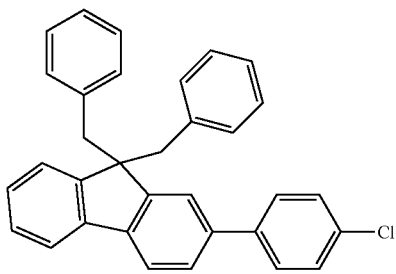

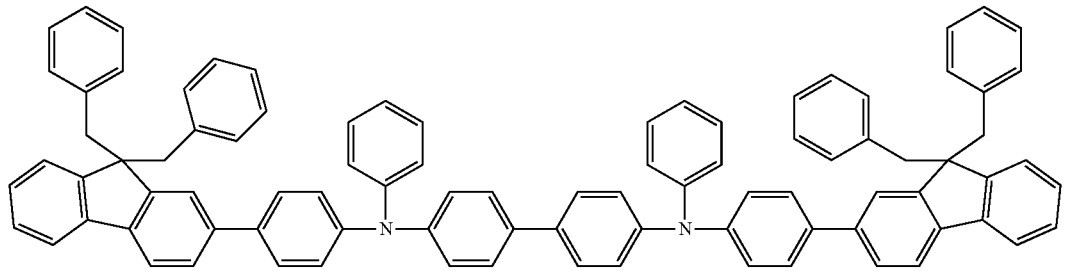

1-2

Comparative Preparation Example 3. Preparation of Chemical Formula 1-3

The following Chemical Formula 1-3 was prepared in the same manner as in Preparation Example 1 except that the following Chemical Formula B-1-8 was used instead of Chemical Formula B-1-1.

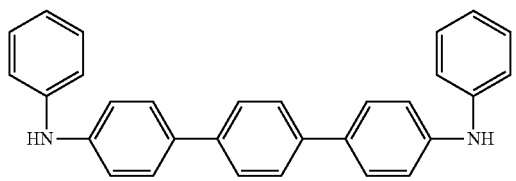

B-1-8

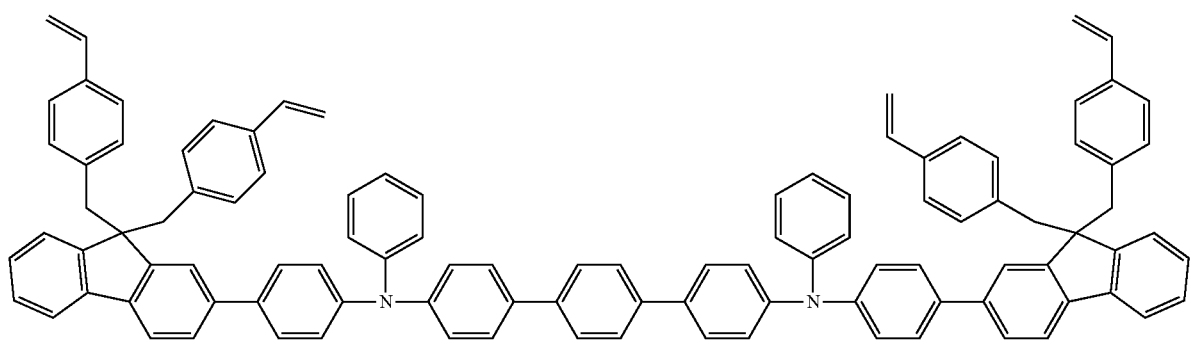

1-3

N,N'-diphenylbenzidine (NPB), 4,4'-bis(2,2-diphenylvinyl) biphenyl (DPVBi), bathophenanthroline (Bphen), LiF and Al were deposited in order. The thicknesses were employed as 20 nm, 50 nm, 20 nm, nm, 0.5 nm and 100 nm, respectively, and the deposition operation was performed after the pressure each became $1 \times 10^{-7}$ torr or less. The deposition rate was 0.01 nm/s to 0.05 nm/s for LiF, and 0.1 nm/s to 0.5 nm/s for the materials other than LiF.

EXAMPLE

Example 1

Under nitrogen atmosphere, 1.4 mL of chlorobenzene was added dropwise to 12.5 mg of the material of Chemical Formula 1-1-1 and the material of Chemical Formula 2-1, and then the result was stirred at room temperature to prepare an ink. The prepared ink was coated on a washed ITO glass substrate, and the result was baked for 1 hour at 200° C. under nitrogen atmosphere to obtain a uniform thin film. This was deposited first by being introduced to a vacuum depositor, and after that, N,N'-di(naphthalene-1-yl)-

Example 2

A device was manufactured in the same manner as in Example 1 except that the material of Chemical Formula 1-1-2 was used instead of Chemical Formula 1-1-1.

Comparative Example 1

A device was manufactured in the same manner as in Example 1 except that the material of Chemical Formula 1-1 was used instead of Chemical Formula 1-1-1.

Comparative Example 2

A device was manufactured in the same manner as in Example 1 except that N,N'-di(naphthalene-1-yl)-N,N'-diphenylbenzidine (NPB) was used instead of Chemical Formula 1-1-1.

Comparative Example 3

A device was manufactured in the same manner as in Example 1 except that the material of Chemical Formula 1-2 was used instead of Chemical Formula 1-1-1.

Comparative Example 4

A device was manufactured in the same manner as in Example 1 except that the material of Chemical Formula 1-3 was used instead of Chemical Formula 1-1-1.

FIG. 2 is a graph showing a relation between a driving voltage and current density for the devices manufactured in Examples 1 and 2 and Comparative Examples 1 and 2. It was identified that the devices of Examples 1 and 2 had a lower driving voltage required for obtaining identical current density compared to the devices of Comparative Examples 1 and 2.

FIG. 3 is a graph showing a relation between a life time and luminance for the devices manufactured in Examples 1 and 2 and Comparative Examples 1 and 2 when the current density was 10 mA/cm². It was identified that, as for the life time, the devices of Comparative Examples 1 and 2 had a rapid decrease in the life time with luminance enhancement compared to the devices of Examples 1 and 2.

FIG. 4 is a graph showing a relation between current density and external quantum efficiency for the devices manufactured in Examples 1 and 2 and Comparative Examples 1 and 2. It was identified that the device of Example 1 had higher external quantum efficiency at the same current density compared to the devices of Comparative Examples 1 and 2.

FIG. 5 is a graph showing a relation between a life time and luminance for the devices manufactured in Example 1, Comparative Example 2 and Comparative Example 4. It was identified that the devices of Comparative Examples 2 and 4 had a rapid decrease in the life time with luminance enhancement compared to the device of Example 1.

FIG. 6 and FIG. 7 are graphs showing wavelength-dependent optical density before/after dipping the devices of Example 1 and Comparative Example 3, respectively, for 10 minutes in a toluene solution after heat treating the devices for 30 minutes at 220° C. It was identified that the device of Comparative Example 3 had a rapid decrease in the optical density after dipping in toluene. Meanwhile, the device of Example 1 maintained optical density even after dipping in toluene. This is due to the fact that the material of Chemical Formula 1-2 used in the device of Comparative Example 3 does not have a curable group and thereby has no solvent resistance. The device of Comparative Example 3 has a problem in that film planarization decreases or interlayer migration occurs between materials since a thin film is not maintained when going through a solution process afterword.

The invention claimed is:

1. A fluorene derivative, a compound represented by the following Chemical Formula 1:

[Chemical Formula 1]

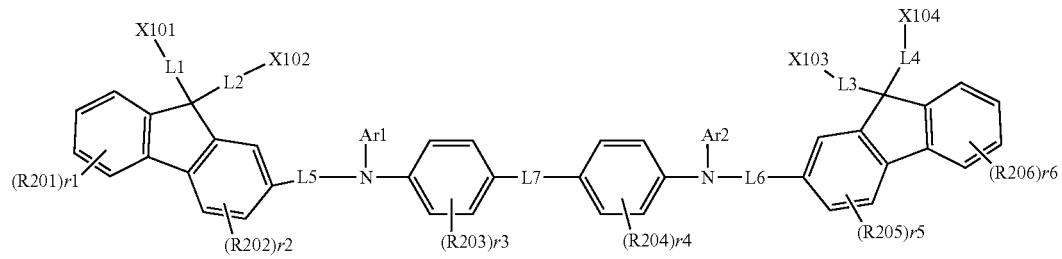

wherein, in Chemical Formula 1,

L1 to L4 are the same as or different from each other, and each independently a direct bond; a substituted or unsubstituted alkylene group; a substituted or unsubstituted cycloalkylene group; a substituted or unsubstituted arylene group; or a substituted or unsubstituted heteroarylene group;

L5 and L6 are the same as or different from each other, and each independently a substituted or unsubstituted arylene group;

L7 is a direct bond, O, S, SO, $SO_2$, or a substituted or unsubstituted alkylene group;

R201 and R206 are the same as or different from each other, and each independently hydrogen; deuterium; a silyl group; a substituted or unsubstituted alkyl group; a substituted or unsubstituted alkenyl group; a substituted or unsubstituted ester group; a substituted or unsubstituted cycloalkyl group; an unsubstituted aryl group; or a substituted or unsubstituted heteroaryl group;

R202 to R205 are the same as or different from each other, and each independently hydrogen; deuterium; a silyl group; a substituted or unsubstituted alkyl group; a substituted or unsubstituted alkenyl group; a substituted or unsubstituted ester group; a substituted or unsubstituted cycloalkyl group; a substituted or unsubstituted aryl group; or a substituted or unsubstituted heteroaryl group;

Ar1 and Ar2 are the same as or different from each other, and each independently a substituted or unsubstituted alkyl group; a substituted or unsubstituted cycloalkyl group; a substituted or unsubstituted aryl group; or a substituted or unsubstituted heteroaryl group;

X101 to X104 are the same as or different from each other, and each independently hydrogen; a thermo-curable group; or a photo-curable group, and at least one of X101 and X102 and at least one of X103 and X104 are each a thermo-curable group; or a photo-curable group;

r1, r3, r4 and r6 are each independently an integer of 0 to 4;

r2 and r5 are each independently an integer of 0 to 3; and when r1 to r6 are each 2 or greater, each of R201 to R206 is dependently the same as or different from each other.

2. The fluorene derivative of claim 1, wherein L5 and L6 are the same as or different from each other, and each independently a phenylene group; a biphenylylene group; a naphthylene group; or a phenanthrenyl group.

3. The fluorene derivative of claim 1, wherein the thermo-curable group or the photo-curable group is selected from among the following structures:

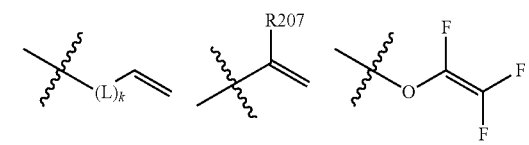

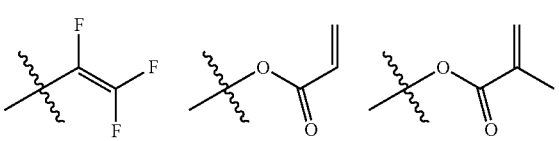

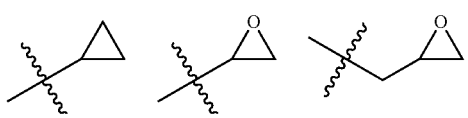

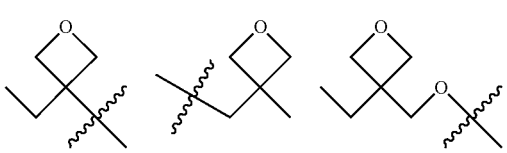

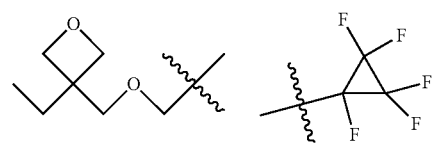

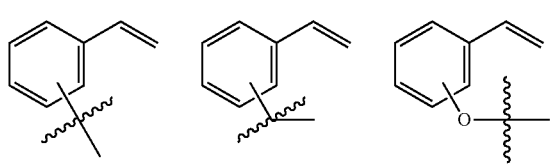

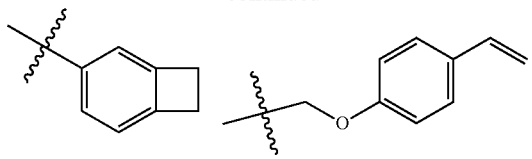

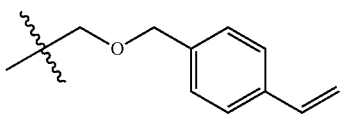

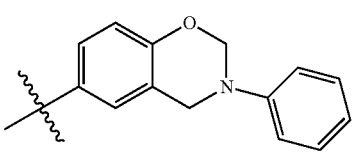

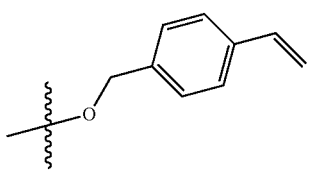

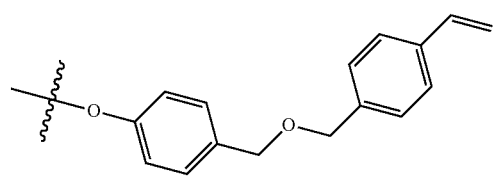

in the structures,

R207 is hydrogen; deuterium; a halogen group; a substituted or unsubstituted alkyl group; a substituted or unsubstituted cycloalkyl group; a substituted or unsubstituted amine group; a substituted or unsubstituted arylamine group; a substituted or unsubstituted silyl group; a substituted or unsubstituted aryl group; or a substituted or unsubstituted heterocyclic group;

L is a direct bond; O; S; a substituted or unsubstituted alkylene group; a substituted or unsubstituted arylene group; or a substituted or unsubstituted divalent a heterocyclic group; and k is an integer of 1 or 2, and when k is 2, each of L is independently the same as or different from each other.

4. The fluorene derivative of claim 1, wherein the compound represented by Chemical Formula 1 is represented by any one of the following 1-1-1 to 1-1-7:

[Chemical Formula 1-1-1]
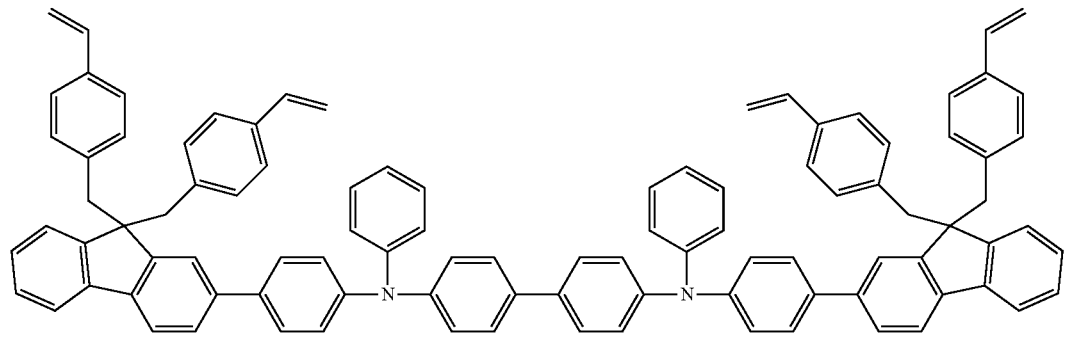
[Chemical Formula 1-1-2]
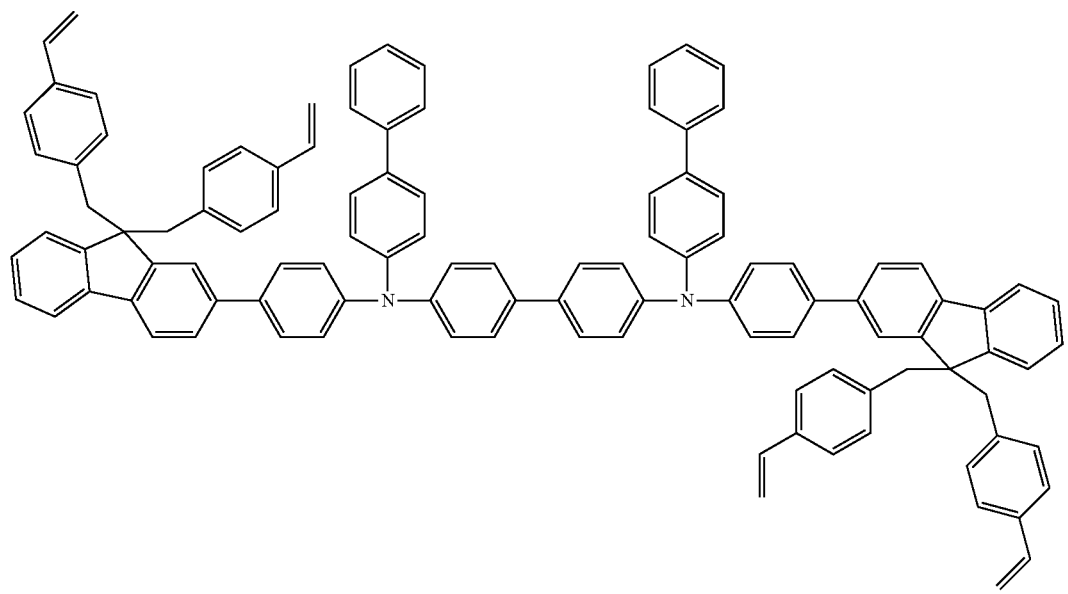
[Chemical Formula 1-1-3]
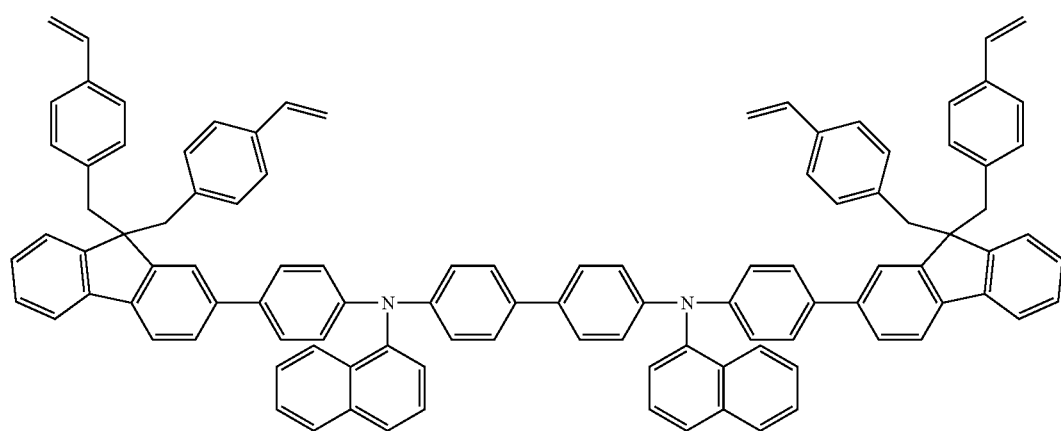

[Chemical Formula 1-1-4]
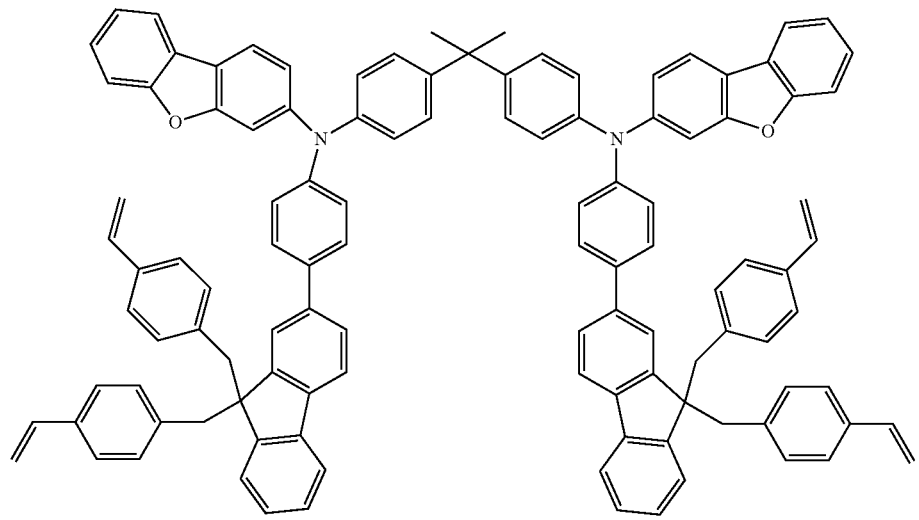
[Chemical Formula 1-1-5]
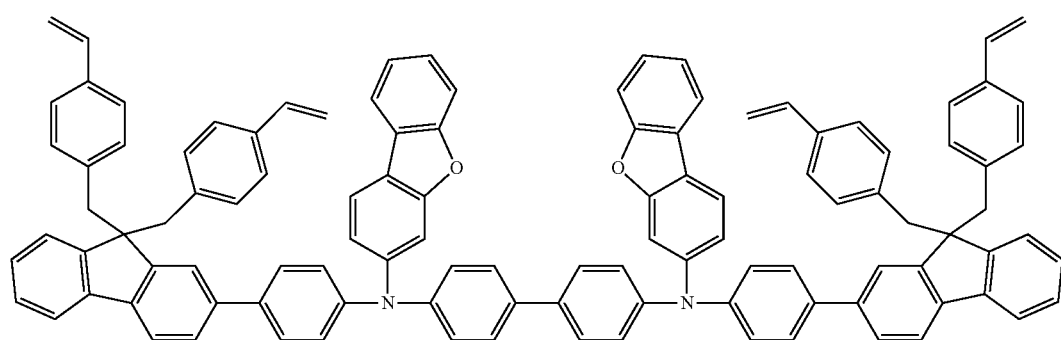
[Chemical Formula 1-1-6]
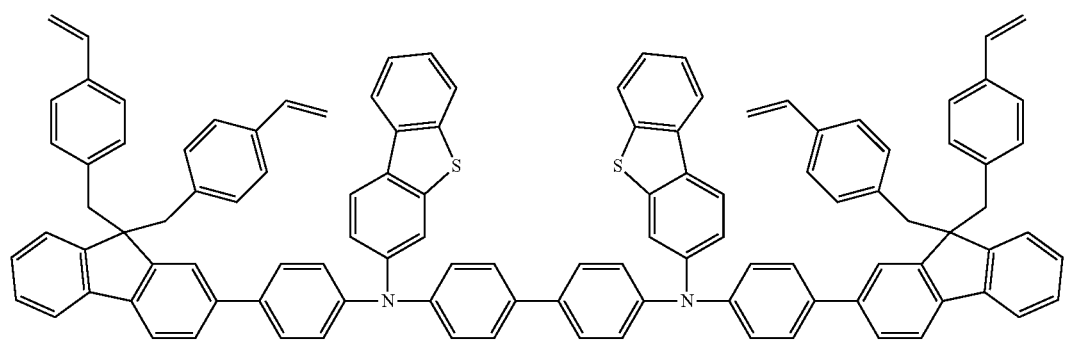
[Chemical Formula 1-1-7]
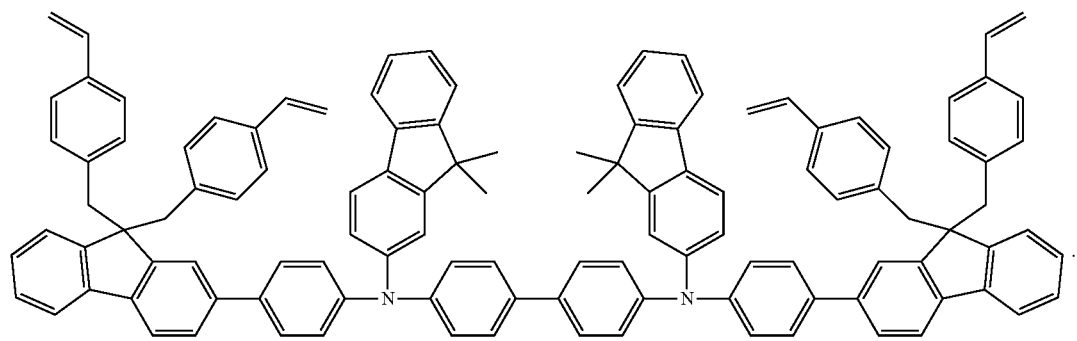

5. A coating composition comprising the fluorene derivative of claim 1.

6. The coating composition of claim 5, further comprising a p-doping material represented by any one of the following structures:

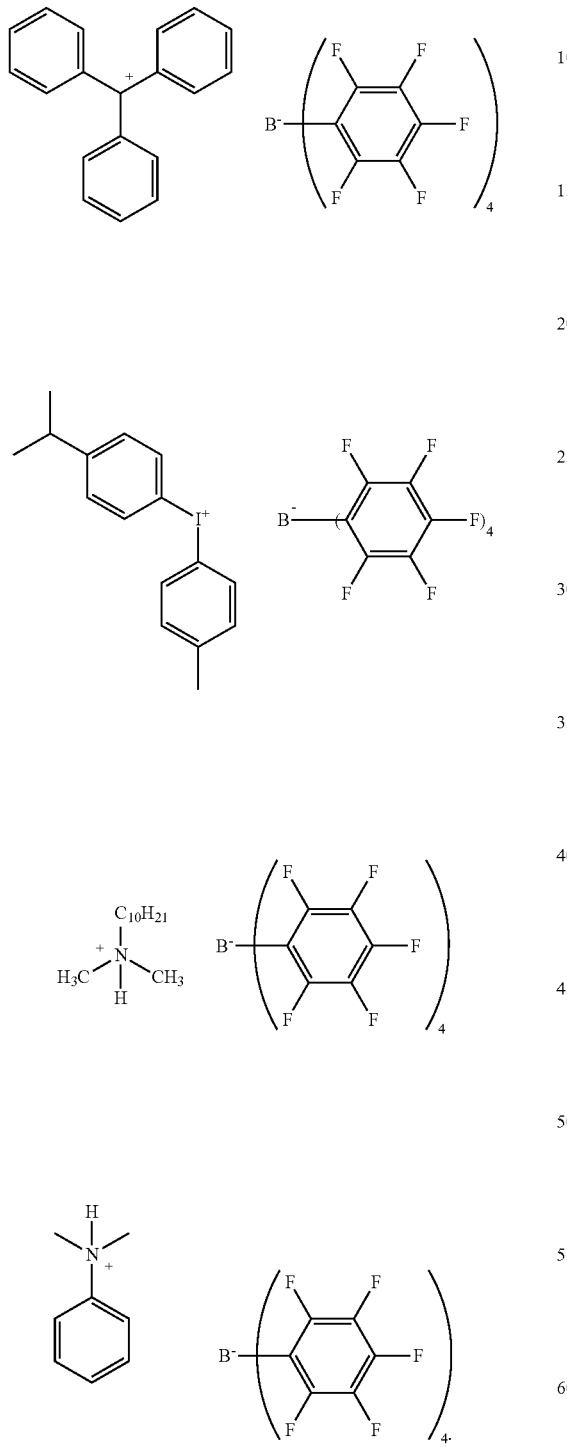

7. The coating composition of claim 5, further comprising a p-doping material including an anionic group represented by the following Chemical Formula 2:

[Chemical Formula 2]

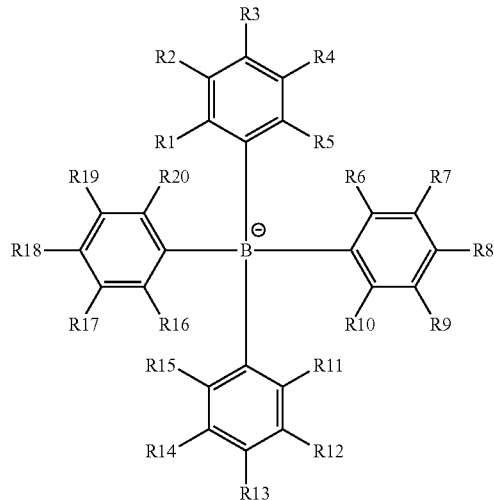

wherein, in Chemical Formula 2, at least one of R1 to R20 is F, a cyano group, or a substituted or unsubstituted fluoroalkyl group;

at least one of the remaining R1 to R20 is a thermo-curable group or a photo-curable group;

the remaining R1 to R20 if present are the same as or different from each other, and each independently hydrogen; deuterium; a nitro group; —C(O)R$_{100}$; —OR$_{101}$; —SR$_{102}$; —SO$_3$R$_{103}$; —COOR$_{104}$; —OC(O)R$_{105}$; —C(O)NR$_{106}$R$_{107}$; a substituted or unsubstituted alkyl group; a substituted or unsubstituted fluoroalkyl group; a substituted or unsubstituted alkenyl group; a substituted or unsubstituted alkynyl group; a substituted or unsubstituted amine group; a substituted or unsubstituted aryl group; or a substituted or unsubstituted heterocyclic group; and R$_{100}$ to R$_{107}$ are the same as or different from each other, and each independently hydrogen; deuterium; or a substituted or unsubstituted alkyl group.

8. The coating composition of claim 7, wherein the thermo-curable group or the photo-curable group is selected from among the following structures:

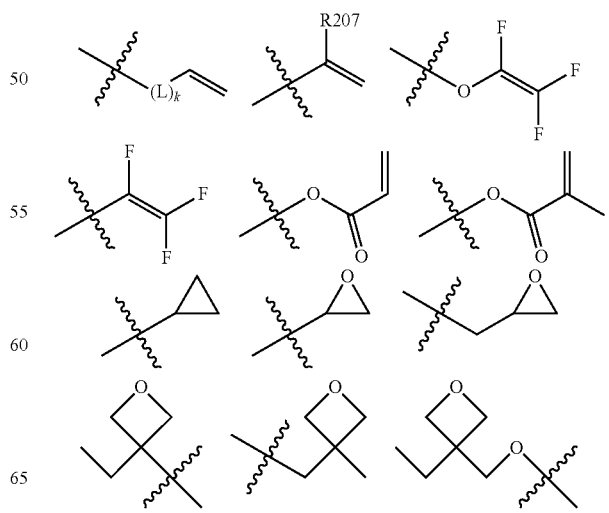

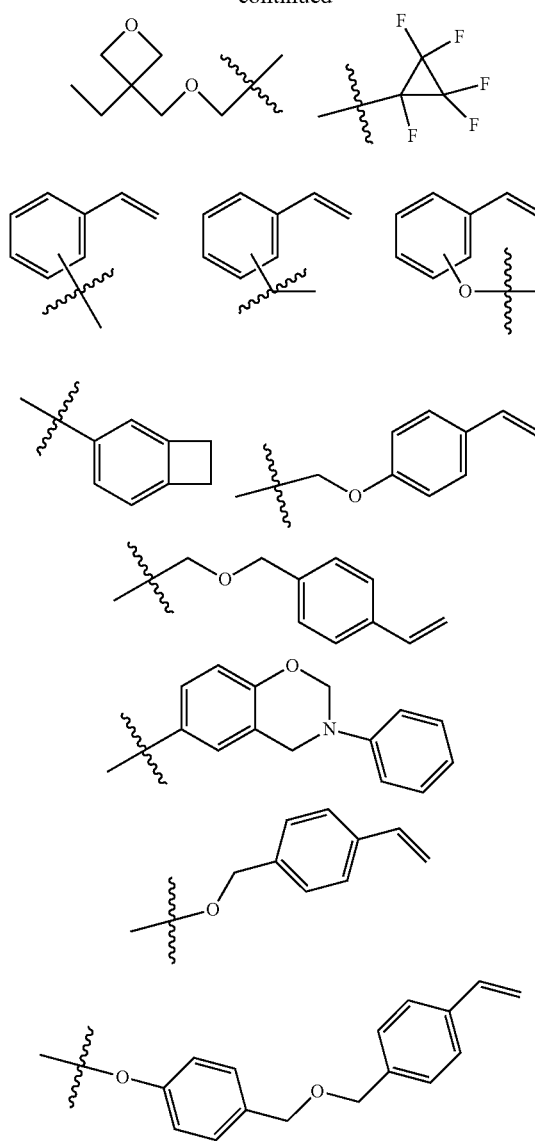
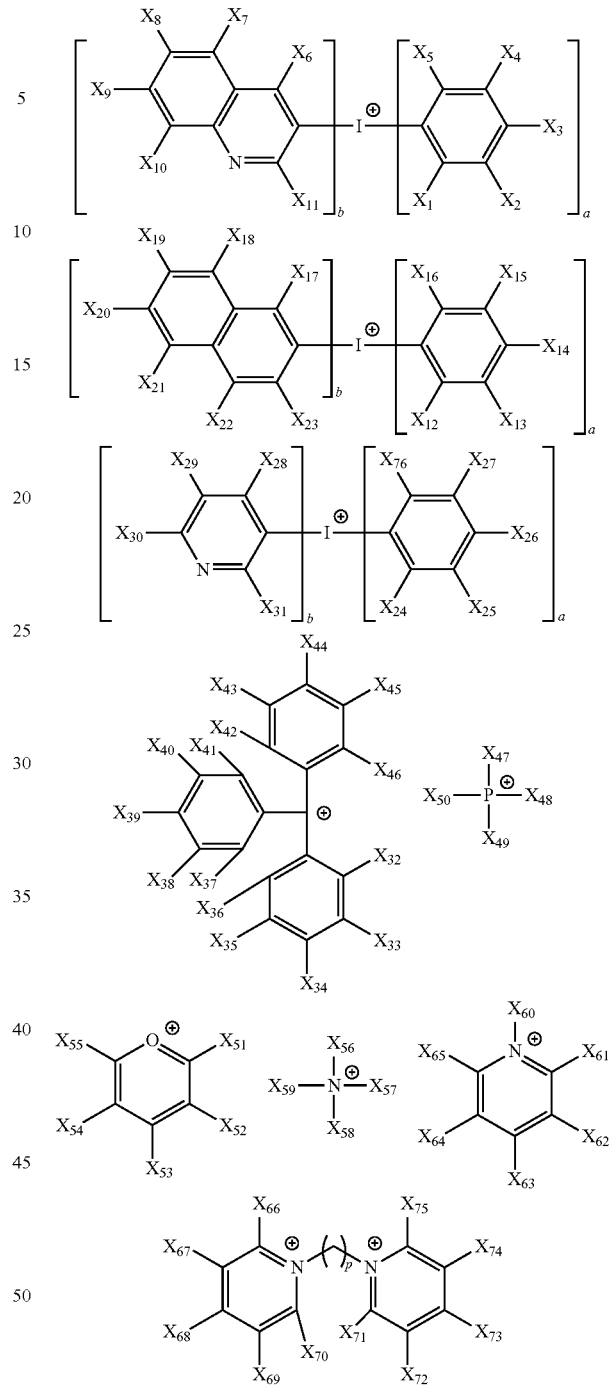

in the structures,

R207 is hydrogen; deuterium; a halogen group; a substituted or unsubstituted alkyl group; a substituted or unsubstituted cycloalkyl group; a substituted or unsubstituted amine group; a substituted or unsubstituted arylamine group; a substituted or unsubstituted silyl group; a substituted or unsubstituted aryl group; or a substituted or unsubstituted heterocyclic group;

L is a direct bond; O; S; a substituted or unsubstituted alkylene group; a substituted or unsubstituted arylene group; or a substituted or unsubstituted divalent heterocyclic group; and k is an integer of 1 or 2, and when k is 2, each of L is independently the same as or different from each other.

9. The coating composition of claim 7, wherein the p-doping material further includes a cationic group, and the cationic group is selected from among monovalent cation groups, onium compounds or the following structural formulae:

in the structural formulae, $X_1$ to $X_{76}$ are the same as or different from each other, and each independently hydrogen; a cyano group; a nitro group; a halogen group; —COOR$_{108}$; a substituted or unsubstituted alkyl group; a substituted or unsubstituted alkoxy group; a substituted or unsubstituted cycloalkyl group; a substituted or unsubstituted fluoroalkyl group; or a substituted or unsubstituted aryl group, or a thermo-curable group or a photo-curable group;

$R_{108}$ is hydrogen; deuterium; or a substituted or unsubstituted alkyl group;

p is an integer of 0 to 10; and a is 1 or 2, b is 0 or 1, and a+b=2.

10. The coating composition of claim 7, wherein the p-doping material is present from 1% by weight to 50% by weight based on the fluorene derivative of Chemical Formula 1.

11. An organic light emitting device comprising:
a cathode;
an anode; and
one or more organic material layers provided between the cathode and the anode,
wherein one or more layers of the organic material layers include a cured material of the coating composition of claim 5, and
the cured material of the coating composition is in a cured state by heat treatment or light treatment on the coating composition.

12. The organic light emitting device of claim 11, wherein the organic material layer including the cured material of the coating composition is a hole transfer layer, a hole injection layer, or a layer carrying out hole transfer and hole injection at the same time.

13. A method for manufacturing an organic light emitting device comprising:
preparing a substrate;
forming a cathode or an anode on the substrate;
forming one or more organic material layers on the cathode or the anode; and
forming an anode or a cathode on the organic material layer,
wherein the forming of one or more organic material layers includes forming an organic material layer using the coating composition of claim 5.

14. The method for manufacturing an organic light emitting device of claim 13, wherein the forming of an organic material layer using the coating composition includes coating the coating composition on the cathode or the anode; and heat treating or light treating the coated coating composition.

15. The coating composition of claim 5, further comprising one or two types of compounds selected from the group consisting of a compound having a thermo-curable group or a photo-curable group introduced into the molecule and a polymer compound.

16. The coating composition of claim 5, further comprising a p-doping material represented by any one of the following structures:

[Chemical Formula 2-1-1]

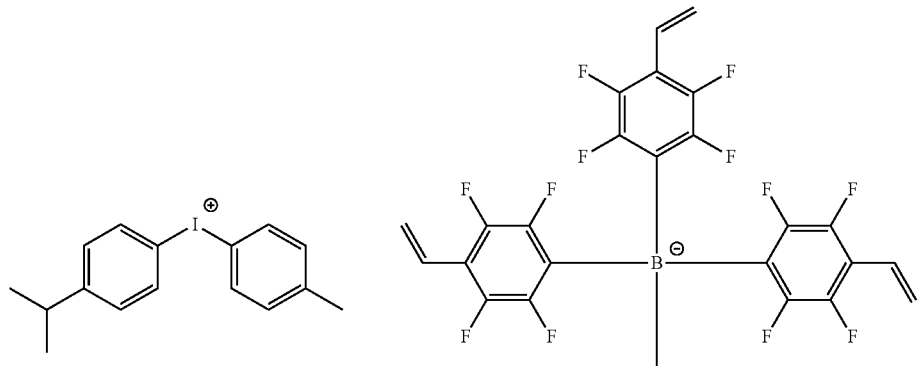

[Chemical Formula 2-1-2]

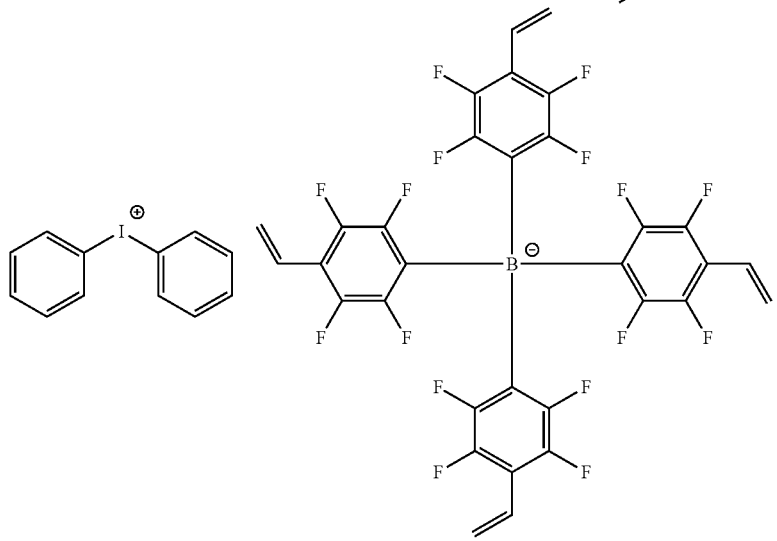

[Chemical Formula 2-1-3]
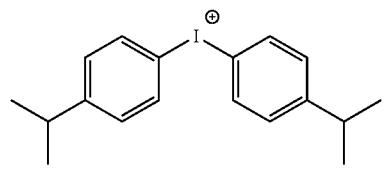 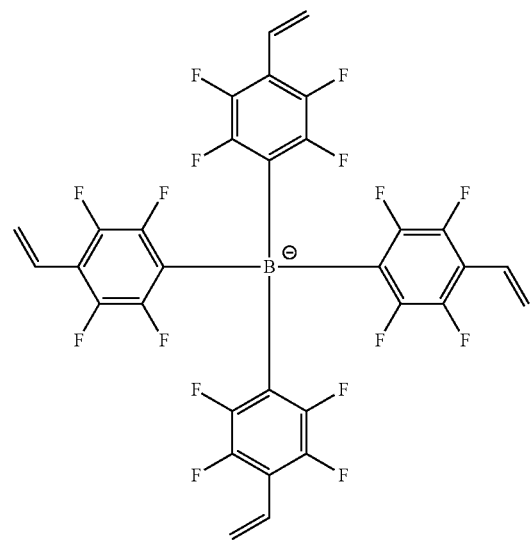
[Chemical Formula 2-1-4]
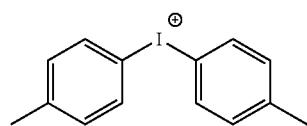 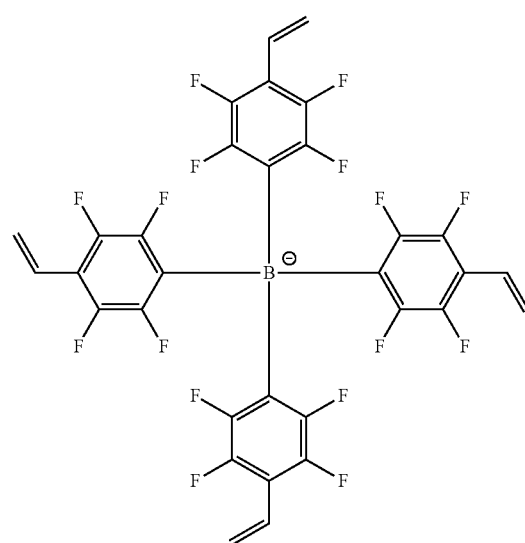
[Chemical Formula 2-1-5]
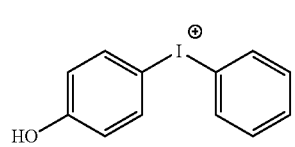 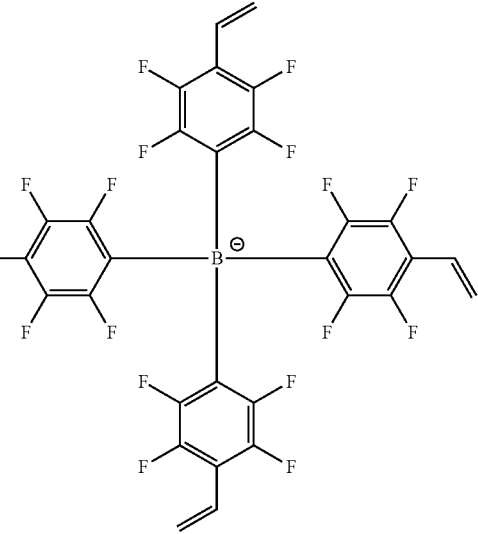

-continued
[Chemical Formula 2-1-6]
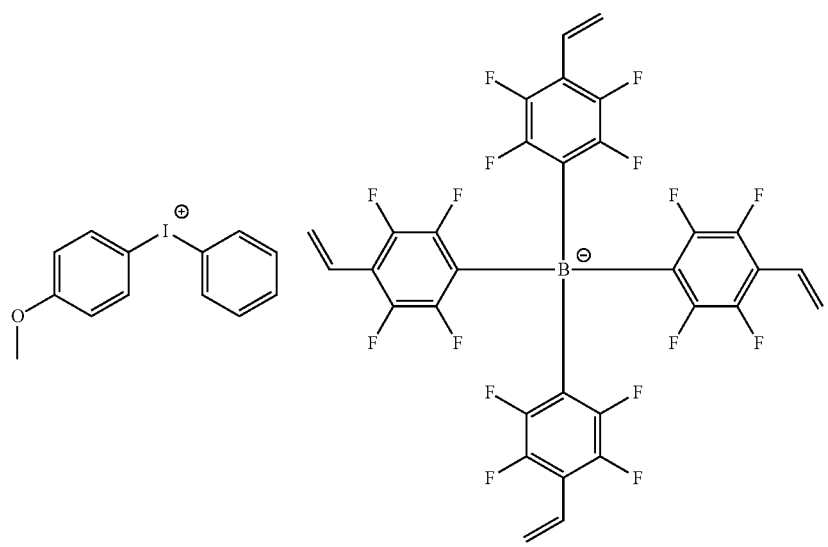
[Chemical Formula 2-1-7]
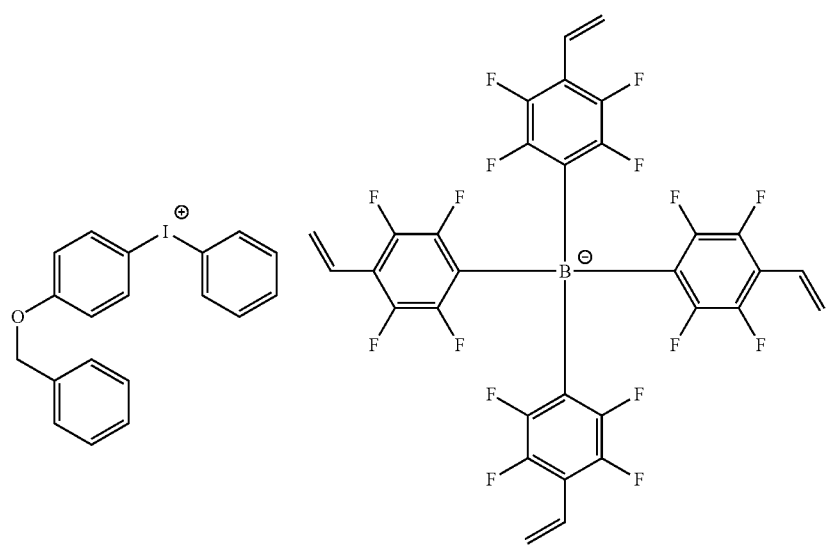
[Chemical Formula 2-1-8]
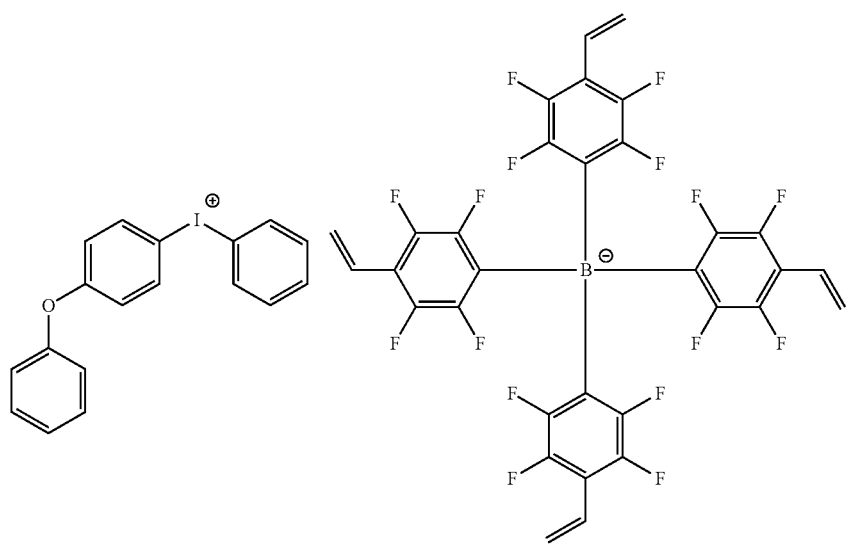

-continued
[Chemical Formula 2-1-9]
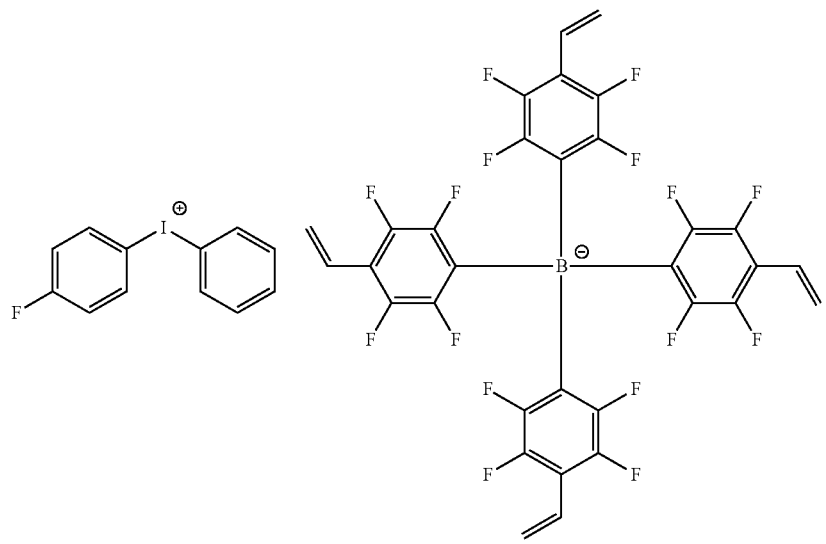
[Chemical Formula 2-1-10]
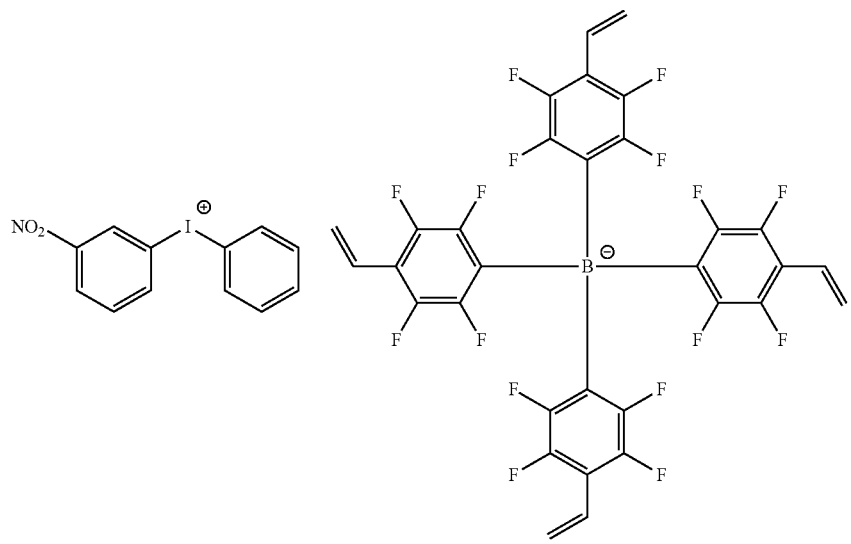
[Chemical Formula 2-1-11]
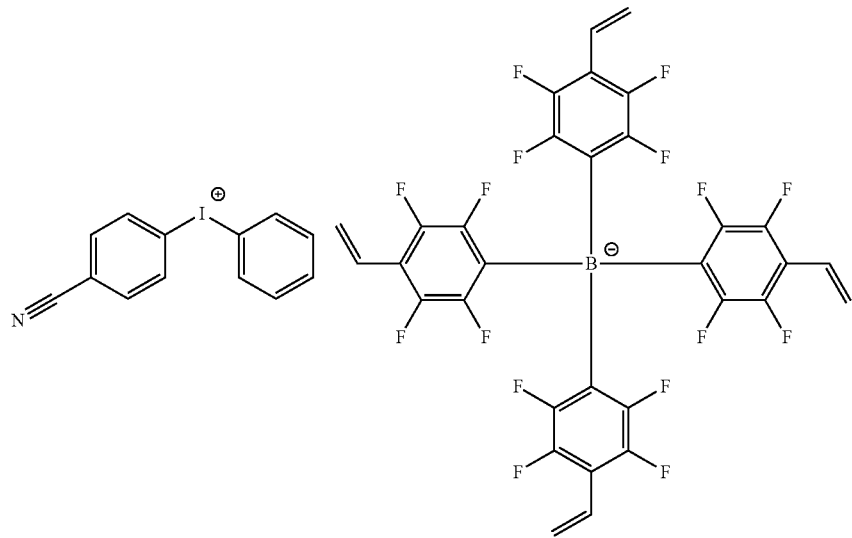

[Chemical Formula 2-1-12]
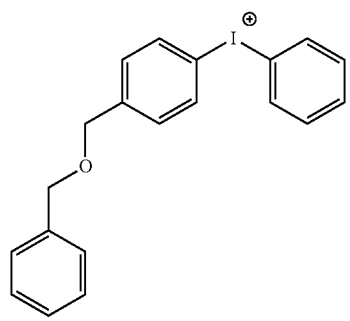 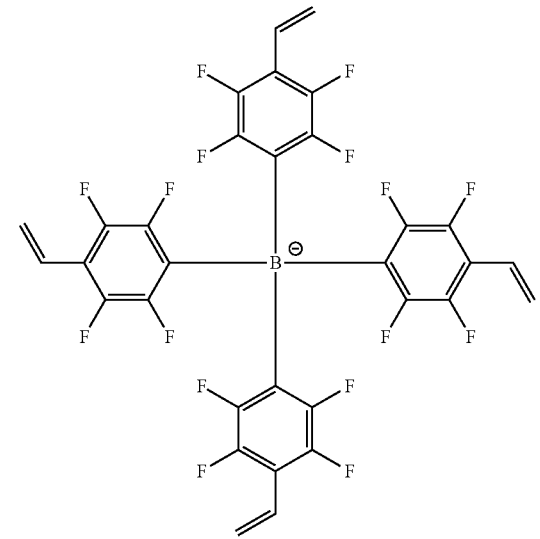
[Chemical Formula 2-1-13]
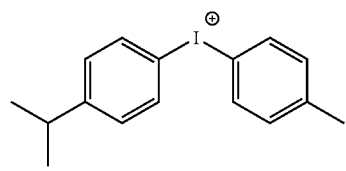 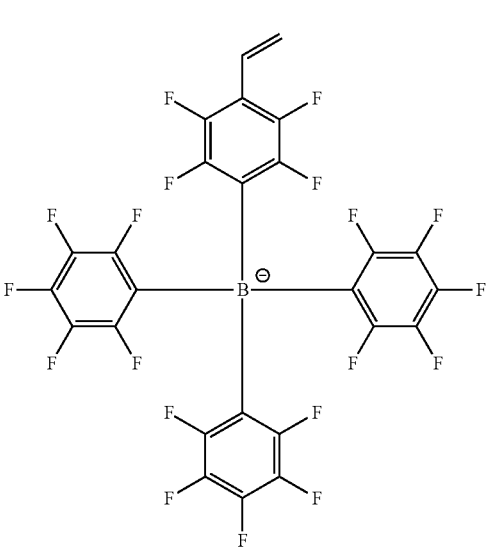
[Chemical Formula 2-1-14]
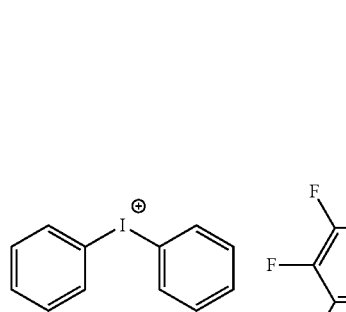 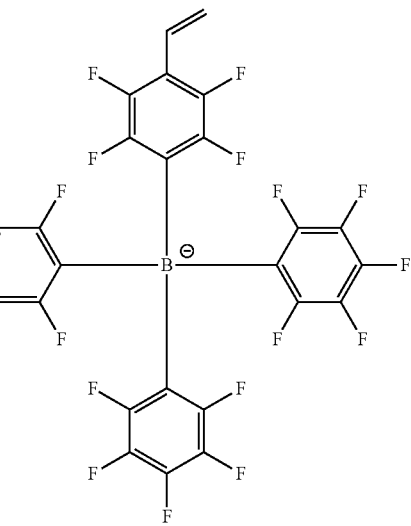

[Chemical Formula 2-1-15]
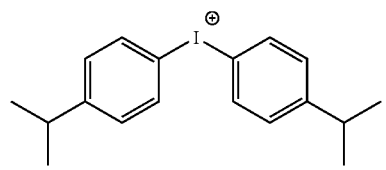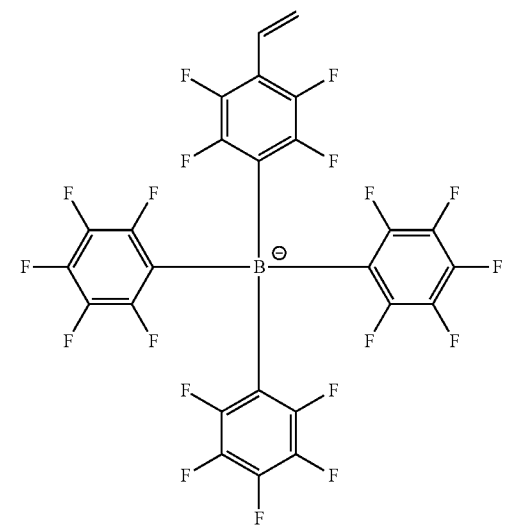
[Chemical Formula 2-1-16]
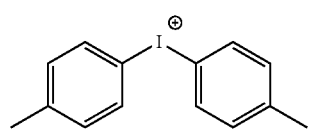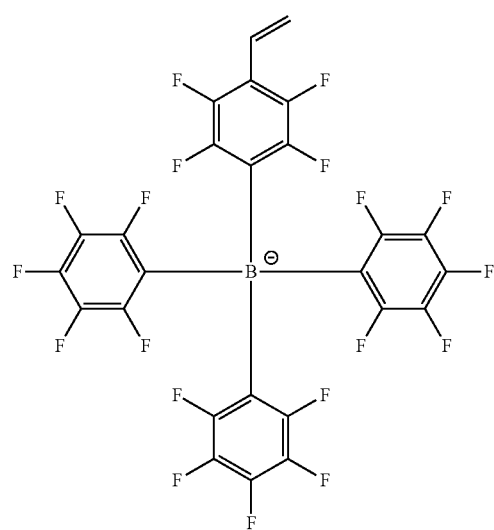
[Chemical Formula 2-1-17]
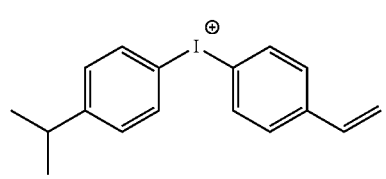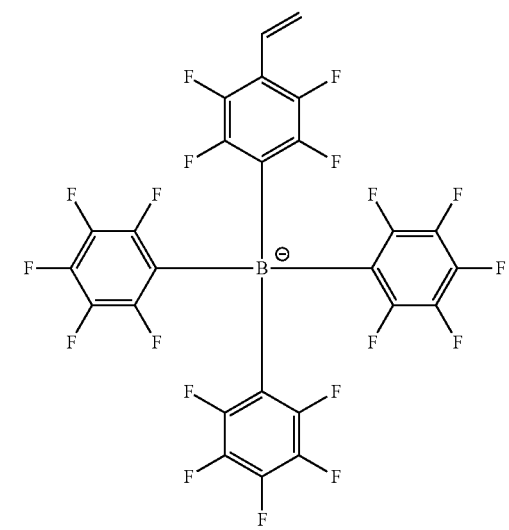

-continued
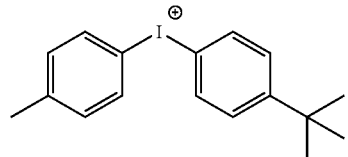
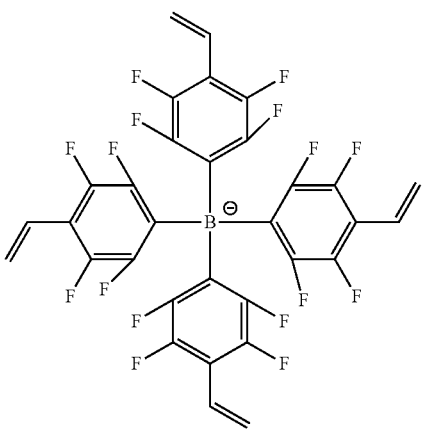
[Chemical Formula 2-1-18]
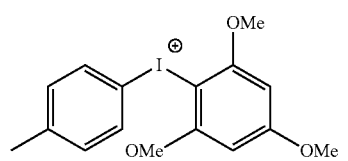
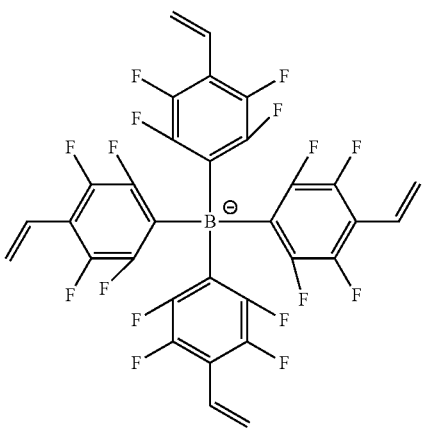
[Chemical Formula 2-1-19]
[Chemical Formula 2-1-20]
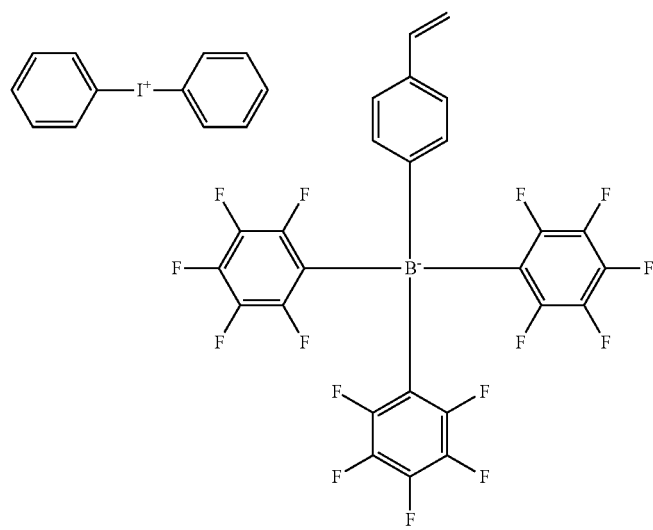

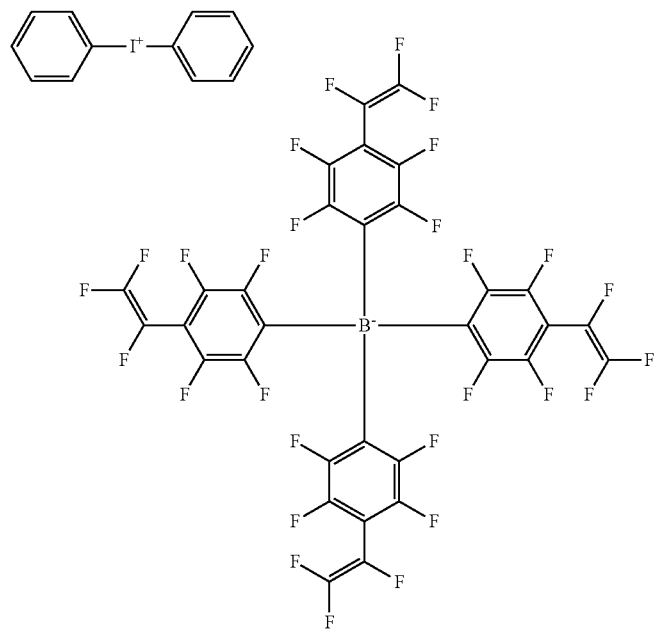
[Chemical Formula 2-1-21]
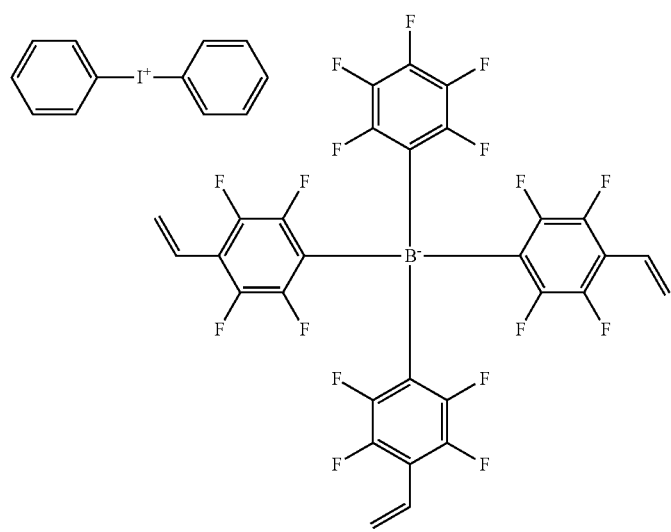
[Chemical Formula 2-1-22]

[Chemical Formula 2-1-23]
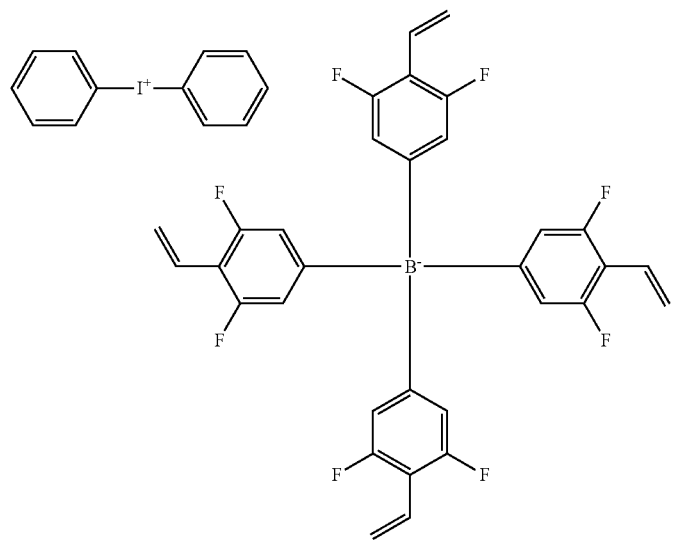
[Chemical Formula 2-1-24]
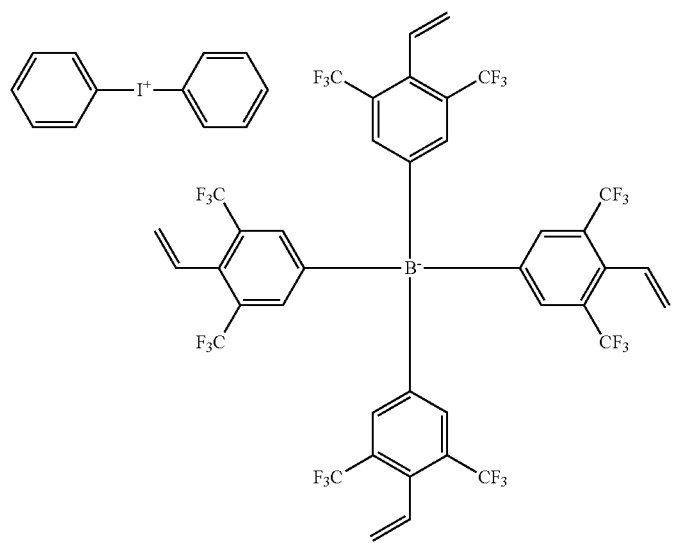

[Chemical Formula 2-1-25]

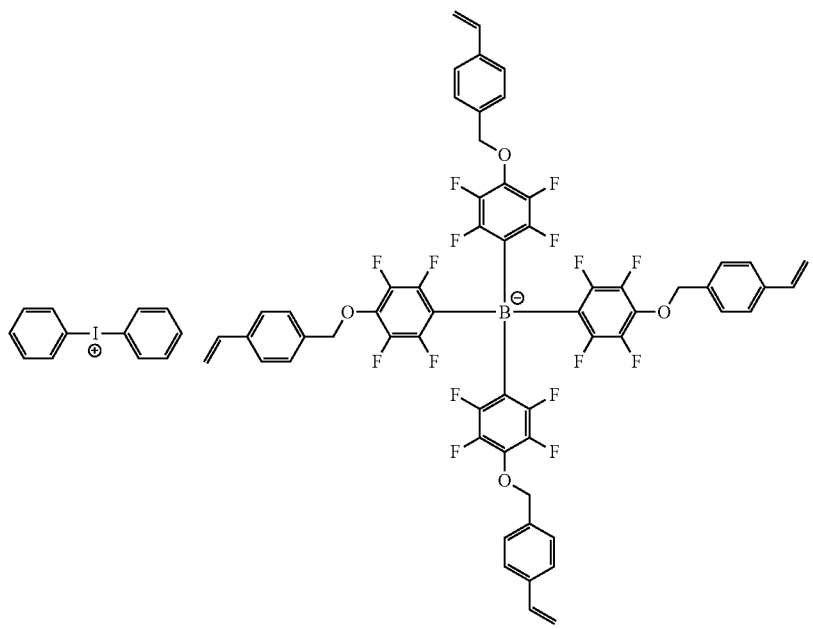

[Chemical Formula 2-1-26]

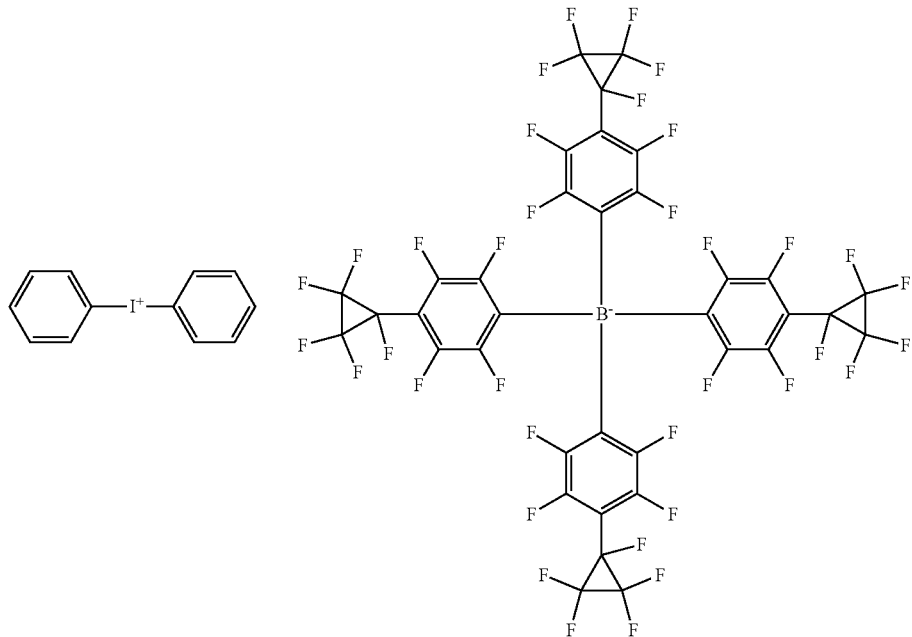

17. The fluorene derivative of claim 1, wherein L1 to L4 are the same as or different from each other, and each independently a direct bond; or a substituted or unsubstituted alkylene group having 1 to 40 carbon atoms.

18. The fluorene derivative of claim 1, wherein L7 is a direct bond, or a substituted or unsubstituted alkylene group having 1 to 40 carbon atoms.

19. The fluorene derivative of claim 1, wherein R201 and R206 are the same as or different from each other, and each independently hydrogen; deuterium; a substituted or unsubstituted alkyl group having 1 to 20 carbon atoms; or an unsubstituted aryl group having 6 to 30 carbon atoms, and R202 to R205 are the same as or different from each other, and each independently hydrogen; deuterium; a substituted or unsubstituted alkyl group having 1 to 20 carbon atoms; or a substituted or unsubstituted aryl group having 6 to 30 carbon atoms.

20. The fluorene derivative of claim 1, wherein Ar1 and Ar2 are the same as or different from each other, and each independently a substituted or unsubstituted phenyl group; a substituted or unsubstituted biphenyl group; a substituted or unsubstituted naphthylenyl group; a substituted or unsubstituted dimethylfluorenyl group; a substituted or unsubstituted dibenzothiophene group; or a substituted or unsubstituted dibenzofuranyl group.

* * * * *